(12) United States Patent
Old et al.

(10) Patent No.: US 7,405,240 B2
(45) Date of Patent: Jul. 29, 2008

(54) SUBSTITUTED CYCLOPENTANES OR CYCLOPENTANONES AS THERAPEUTIC AGENTS

(75) Inventors: David W. Old, Irvine, CA (US); Todd S. Gac, Irvine, CA (US); Vinh X. Ngo, Huntington Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 11/971,449

(22) Filed: Jan. 9, 2008

(65) Prior Publication Data

US 2008/0119560 A1    May 22, 2008

Related U.S. Application Data

(63) Continuation of application No. 11/619,997, filed on Jan. 4, 2007, now Pat. No. 7,323,591.

(60) Provisional application No. 60/757,696, filed on Jan. 10, 2006.

(51) Int. Cl.
    *A61K 31/5575*    (2006.01)

(52) U.S. Cl. .................................................. 514/573
(58) Field of Classification Search ............... None
    See application file for complete search history.

(56) References Cited

U.S. PATENT DOCUMENTS

| 3,980,700 | A | | 9/1976 | Miyano |
| 4,233,296 | A | | 11/1980 | Teutsch et al. |
| 4,806,668 | A | * | 2/1989 | Raduechel et al. .......... 556/436 |
| 6,426,359 | B1 | | 7/2002 | Cameron et al. |

FOREIGN PATENT DOCUMENTS

| HU | 46301 A2 | 10/1988 |
| JP | 2001163779 | 6/2001 |
| WO | WO98/27976 | 7/1998 |
| WO | WO98/58911 | 12/1998 |
| WO | WO2003/074483 | 9/2003 |
| WO | WO2004/089411 | 10/2004 |

* cited by examiner

*Primary Examiner*—Paul A Zucker
(74) *Attorney, Agent, or Firm*—Allergan, Inc.; Martin Voet; Brent A. Johnson

(57) ABSTRACT

The compounds disclosed herein are useful for treating glaucoma, ocular hypertension, and baldness.

24 Claims, 6 Drawing Sheets

22aa (para)
22gg (meta)

22bb-ff (para)
22hh-mm (meta)

22cc

23cc (R=H)
23dd (R=Me)

22ee(R=n-pentyl)
22ff (R=Me)

23ee(R=n-pentyl)
23ff (R=Me)

25a (ortho)
25b (meta)

26a (ortho)
26b (meta)

27a (ortho)
27b (meta)

SUBSTITUTED CYCLOPENTANES OR CYCLOPENTANONES AS THERAPEUTIC AGENTS

CROSS-REFERENCE TO RELATED APPLICATIONS

This application is a continuation of U.S. patent application Ser. No. 11/619,997, filed Jan. 4, 2007 now U.S. Pat. No. 7,323,591, which claims priority under 35 U.S.C. § 120 to Provisional Patent Application No. 60/757,696, filed on Jan. 10, 2006.

DESCRIPTION OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

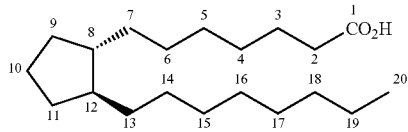

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Prostaglandin $EP_2$ selective agonists are believed to have several medical uses. For example, U.S. Pat. No. 6,437,146 teaches the use of prostaglandin $EP_2$ selective agonists "for treating or preventing inflammation and pain in joint and muscle (e.g., rheumatoid arthritis, rheumatoid spondylitis, osteoarthritis, gouty arthritis, juvenile arthritis, etc.), inflammatory skin condition (e.g., sunburn, burns, eczema, dermatitis, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., aphthous ulcer, Chrohn's disease, atrophic gastritis, gastritis varialoforme, ulcerative colitis, coeliac disease, regional ileitis, irritable bowel syndrome, etc.), gingivitis, inflammation, pain and tumescence after operation or injury, pyrexia, pain and other conditions associated with inflammation, allergic disease, systemic lupus crythematosus, scleroderma, polymyositis, tendinitis, bursitis, periarteritis nodose, rheumatic fever, Sjgren's syndrome, Behcet disease, thyroiditis, type I diabetes, diabetic complication (diabetic microangiopathy, diabetic retinopathy, diabetic neohropathy, etc.), nephrotic syndrome, aplastic anemia, myasthenia gravis, uveitis contact dermatitis, psoriasis, Kawasaki disease, sarcoidosis, Hodgkin's disease, Alzheimers disease, kidney dysfunction (nephritis, nephritic syndrome, etc.), liver dysfunction (hepatitis, cirrhosis, etc.), gastrointestinal dysfunction (diarrhea, inflammatory bowel disease, etc.) shock, bone disease characterized by abnormal bone metabolism such as osteoporosis (especially, postmenopausal osteoporosis), hypercalcemia, hyperparathyroidism, Paget's bone diseases, osteolysis, hypercalcemia of malignancy with or without bone metastases, rheumatoid arthritis, periodonritis, osteoarthritis, ostealgia, osteopenia, cancer cachexia, calculosis, lithiasis (especially, urolithiasis), solid carcinoma, mesangial proliferative glomerulonephritis, edema (e.g. cardiac edema, cerebral edema, etc.), hypertension such as malignant hypertension or the like, premenstrual tension, urinary calculus, oliguria such as the one caused by acute or chronic failure, hyperphosphaturia, or the like."

U.S. Pat. No. 6,710,072 teaches the use of EP2 agonists for the treatment or prevention of "osteoporosis, constipation, renal disorders, sexual dysfunction, baldness, diabetes, cancer and in disorder of immune regulation . . . various pathophysiological diseases including acute myocardial infarction, vascular thrombosis, hypertension, pulmonary hypertension, ischemic heart disease, congestive heart failure, and angina pectoris."

Figure 1:
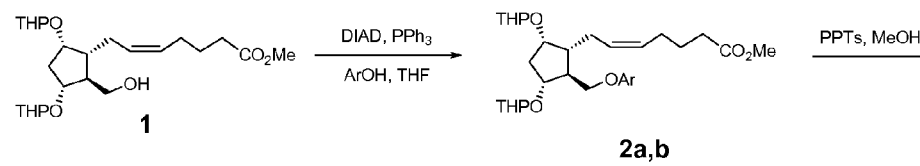
FIG. 1 depicts an exemplary method of preparing certain compounds disclosed herein.
Figure 1:
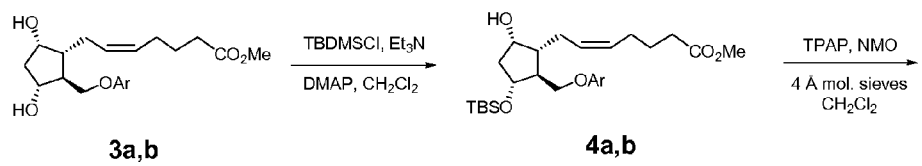
Figure 1:
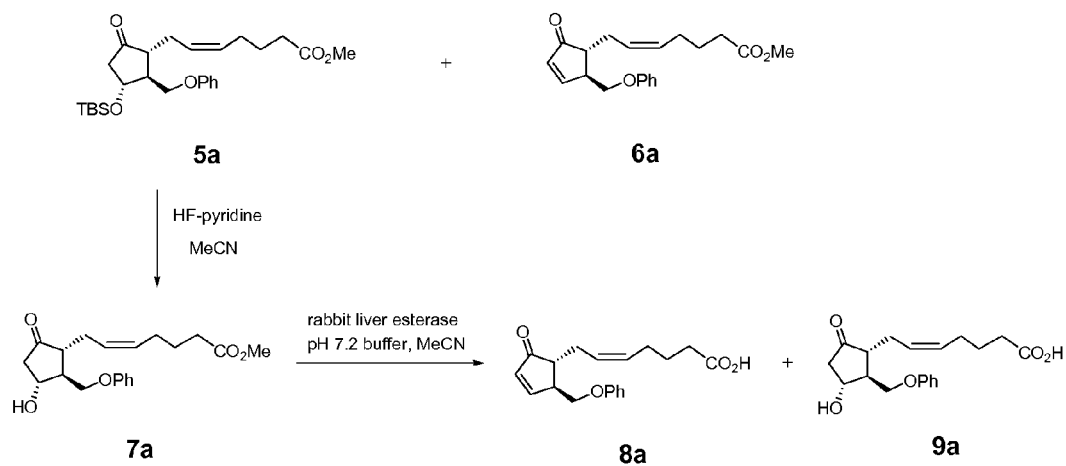

One embodiment is a compound according to the formula

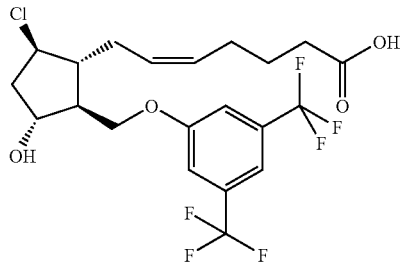

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

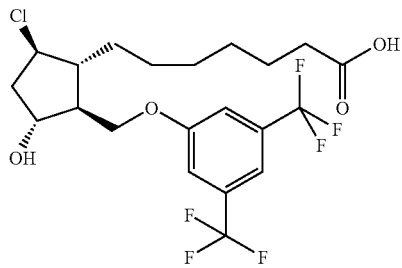

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable. Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

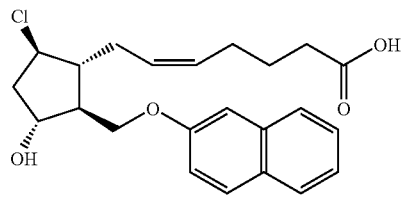

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

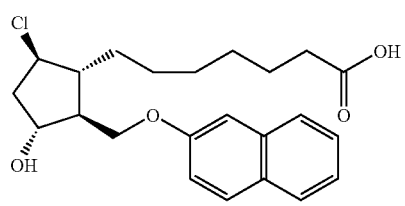

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

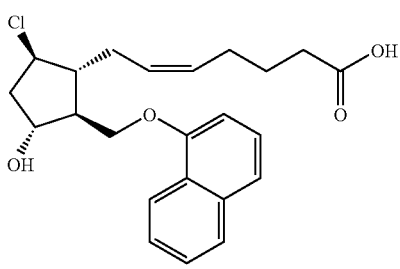

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

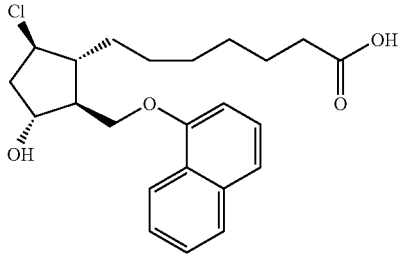

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

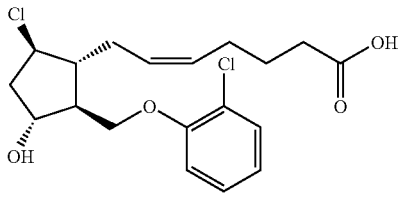

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

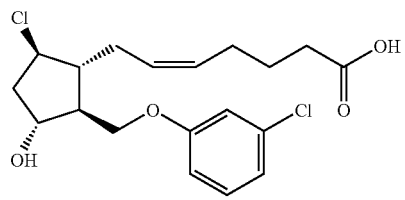

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

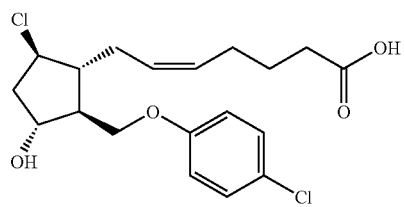

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

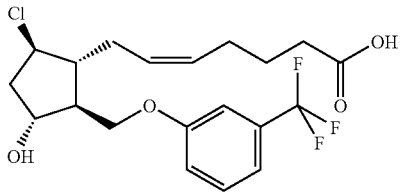

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

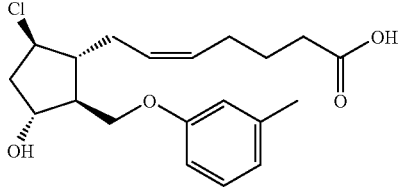

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

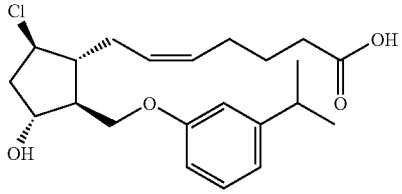

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

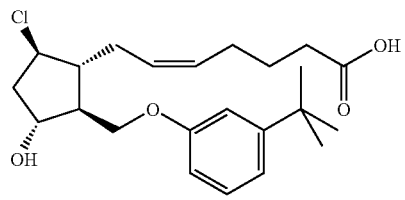

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

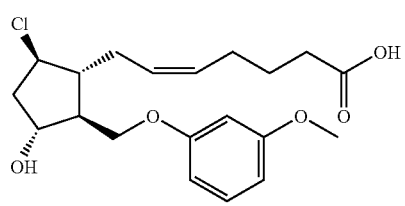

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

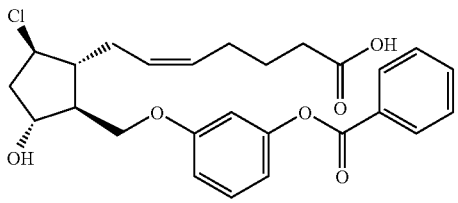

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

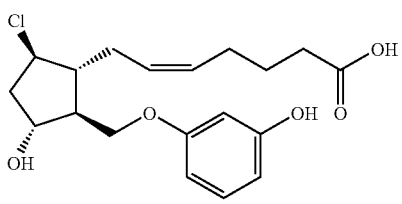

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

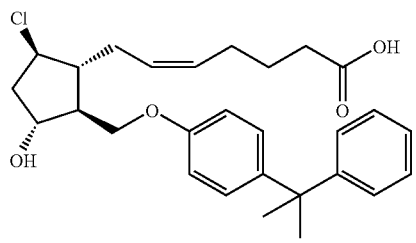

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

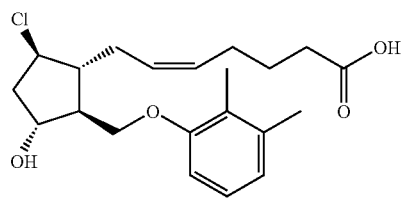

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

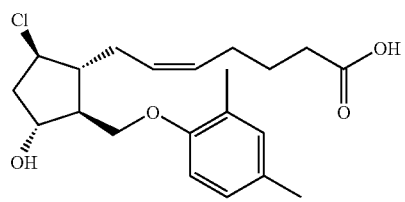

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

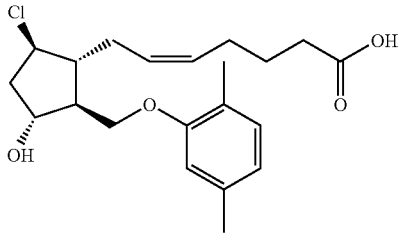

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

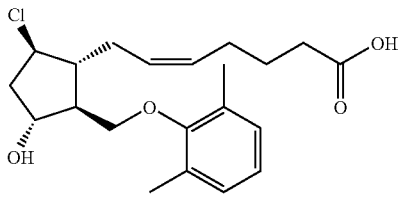

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

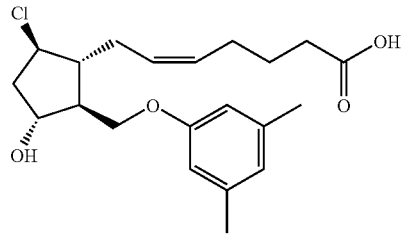

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

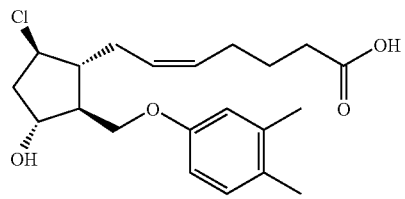

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

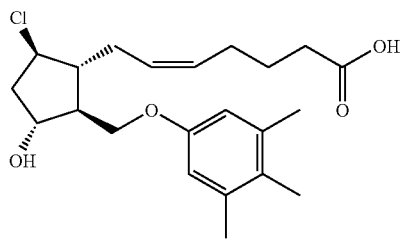

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

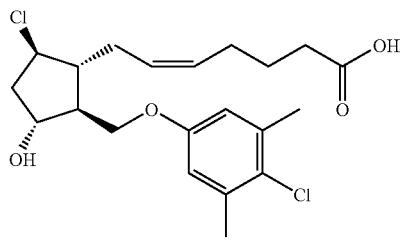

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

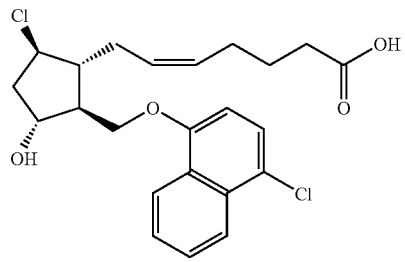

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

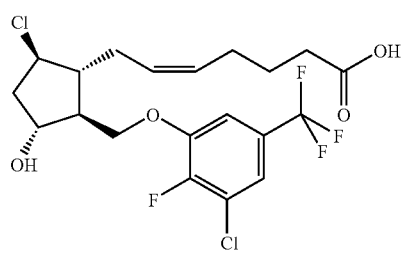

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

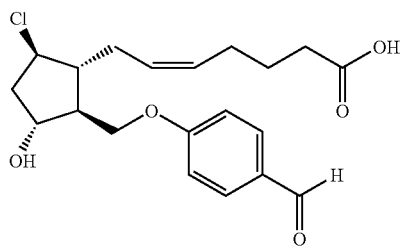

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

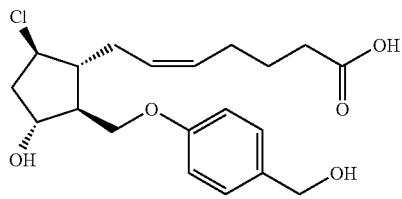

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

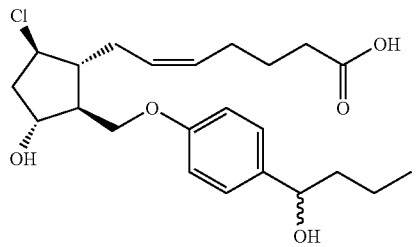

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

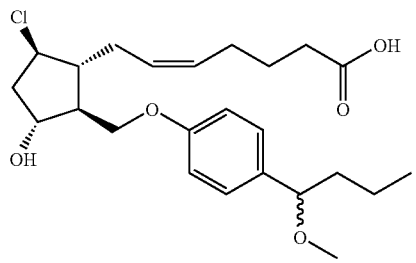

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

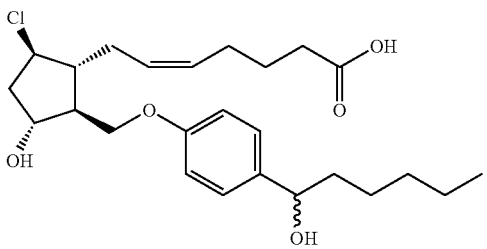

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

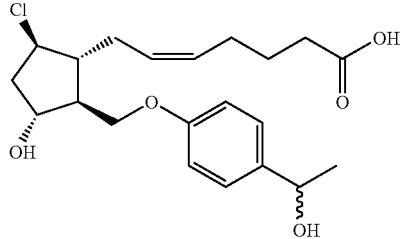

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

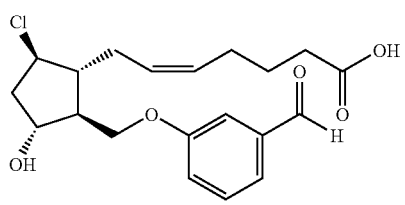

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

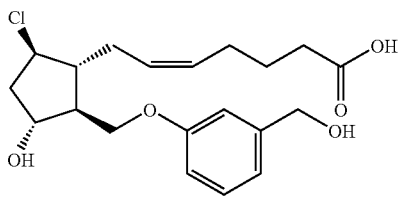

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

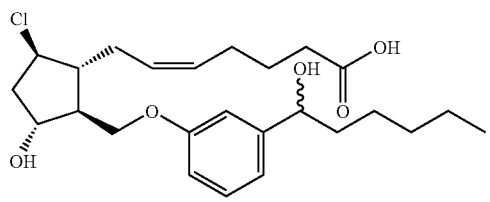

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

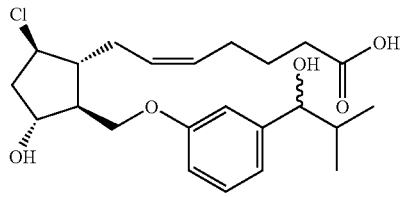

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

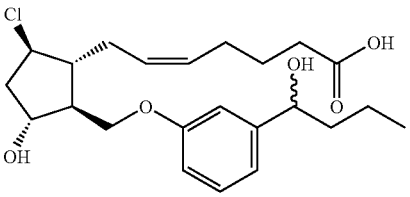

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

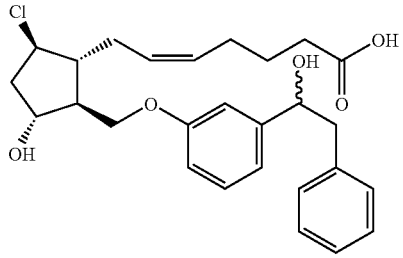

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

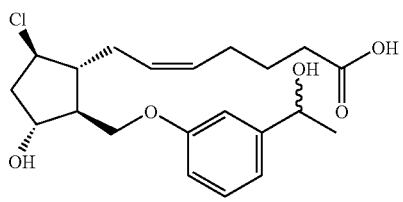

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

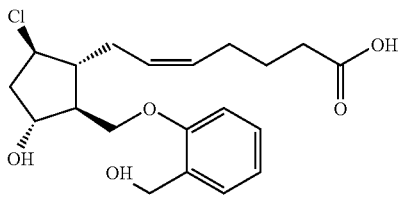

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

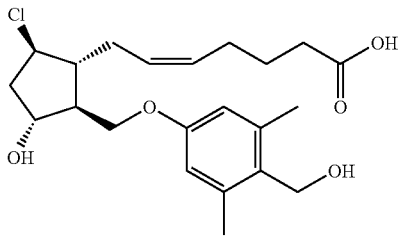

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

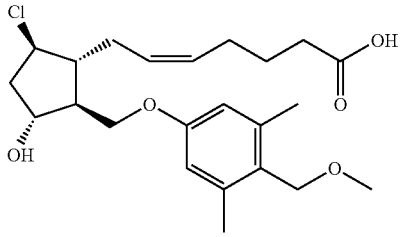

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

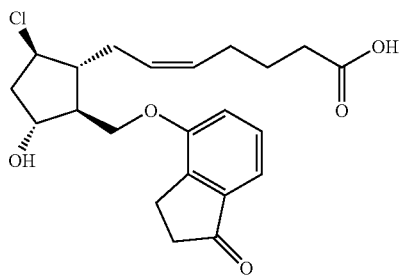

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

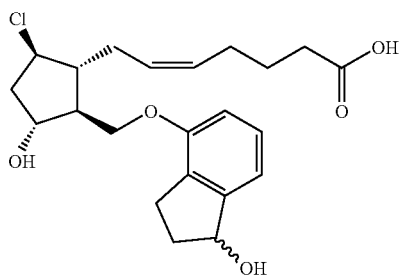

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

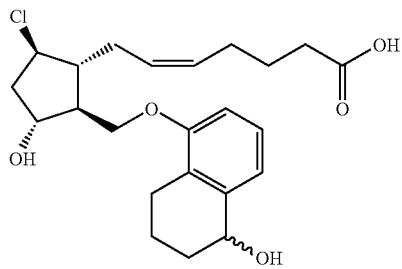

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

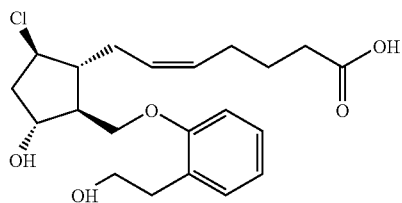

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

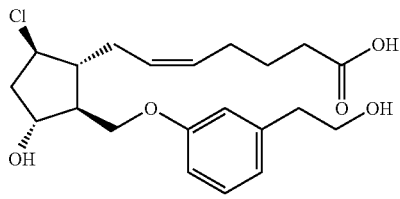

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

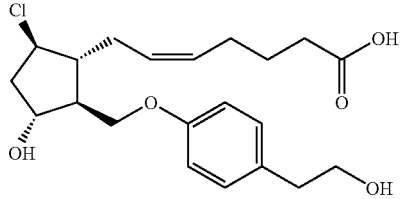

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

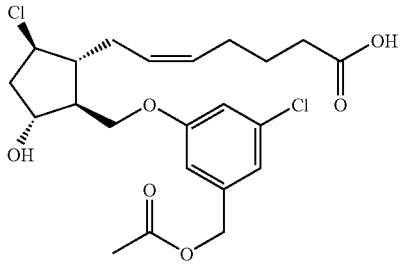

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

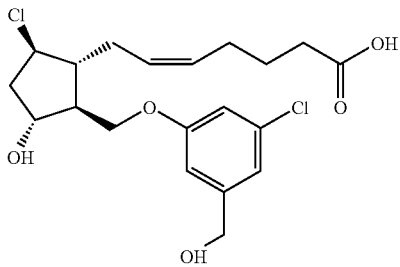

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Another embodiment is a compound according to the formula

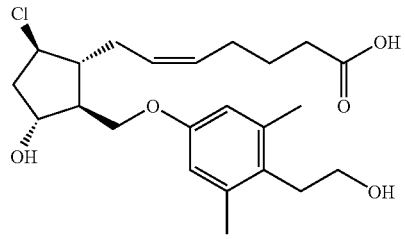

or a pharmaceutically acceptable salt or a prodrug thereof.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

Each of the compounds listed below are individually embodiments.

(Z)-7-[(1R,2S,3R,5R)-2-(3,5-Bis-trifluoromethyl-phenoxymethyl)-5-chloro-3-hydroxy-cyclopentyl]-hept-5-enoic acid;

(Z)-7-[(1R,2S,3R,5R)-2-(3,5-Bis-trifluoromethyl-phenoxymethyl)-5-chloro-3-hydroxy-cyclopentyl]-heptanoic acid;

(Z)-7-[(1R,2S,3R,5R)-5-Chloro-3-hydroxy-2-(naphthalen-2-yloxymethyl)-cyclopentyl]-hept-5-enoic acid;

(Z)-7-[(1R,2S,3R,5R)-5-Chloro-3-hydroxy-2-(naphthalen-2-yloxymethyl)-cyclopentyl]-heptanoic acid;

(Z)-7-[(1R,2S,3R,5R)-5-Chloro-3-hydroxy-2-(naphthalen-1-yloxymethyl)-cyclopentyl]-hept-5-enoic acid;

(Z)-7-[(1R,2S,3R,5R)-5-Chloro-3-hydroxy-2-(naphthalen-1-yloxymethyl)-cyclopentyl]-heptanoic acid;

(Z)-7-[(1R,2S,3R,5R)-5-Chloro-2-(2-chloro-phenoxymethyl)-3-hydroxy-cyclopentyl]-hept-5-enoic acid;

(Z)-7-[(1R,2S,3R,5R)-5-Chloro-2-(3-chloro-phenoxymethyl)-3-hydroxy-cyclopentyl]-hept-5-enoic acid;

(Z)-7-[(1R,2S,3R,5R)-5-Chloro-2-(4-chloro-phenoxymethyl)-3-hydroxy-cyclopentyl]-hept-5-enoic acid;

(Z)-7-[(1R,2S,3R,5R)-5-Chloro-3-hydroxy-2-(3-trifluoromethyl-phenoxymethyl)-cyclopentyl]-hept-5-enoic acid;

(Z)-7-((1R,2S,3R,5R)-5-Chloro-3-hydroxy-2-m-tolyloxymethyl-cyclopentyl)-hept-5-enoic acid;

(Z)-7-[(1R,2S,3R,5R)-5-Chloro-3-hydroxy-2-(3-isopropyl-phenoxymethyl)-cyclopentyl]-hept-5-enoic acid;

(Z)-7-[(1R,2S,3R,5R)-2-(3-tert-Butyl-phenoxymethyl)-5-chloro-3-hydroxy-cyclopentyl]-hept-5-enoic acid;

(Z)-7-[(1R,2S,3R,5R)-5-Chloro-3-hydroxy-2-(3-methoxy-phenoxymethyl)-cyclopentyl]-hept-5-enoic acid;

3-[(S,2R,3R,5R)-2-((Z)-6-carboxy-hex-2-enyl)-3-chloro-5-hydroxy-cyclopentylmethoxy]-phenyl benzoate;

(Z)-7-[(1R,2S,3R,5R)-5-Chloro-3-hydroxy-2-(3-hydroxy-phenoxymethyl)-cyclopentyl]-hept-5-enoic acid;

(Z)-7-{(1R,2S,3R,5R)-5-Chloro-3-hydroxy-2-[4-(1-methyl-1-phenyl-ethyl)-phenoxymethyl]-cyclopentyl}-hept-5-enoic acid;

(Z)-7-[(1R,2S,3R,5R)-5-Chloro-2-(2,3-dimethyl-phenoxymethyl)-3-hydroxy-cyclopentyl]-hept-5-enoic acid;

(Z)-7-[(1R,2S,3R,5R)-5-Chloro-2-(2,4-dimethyl-phenoxymethyl)-3-hydroxy-cyclopentyl]-hept-5-enoic acid;

(Z)-7-[(1R,2S,3R,5R)-5-Chloro-2-(2,5-dimethyl-phenoxymethyl)-3-hydroxy-cyclopentyl]-hept-5-enoic acid;

(Z)-7-[(1R,2S,3R,5R)-5-Chloro-2-(2,6-dimethyl-phenoxymethyl)-3-hydroxy-cyclopentyl]-hept-5-enoic acid;

(Z)-7-[(1R,2S,3R,5R)-5-Chloro-2-(3,5-dimethyl-phenoxymethyl)-3-hydroxy-cyclopentyl]-hept-5-enoic acid;

(Z)-7-[(1R,2S,3R,5R)-5-Chloro-2-(3,4-dimethyl-phenoxymethyl)-3-hydroxy-cyclopentyl]-hept-5-enoic acid;

(Z)-7-[(1R,2S,3R,5R)-5-Chloro-3-hydroxy-2-(3,4,5-trimethyl-phenoxymethyl)-cyclopentyl]-hept-5-enoic acid;

(Z)-7-[(1R,2S,3R,5R)-5-Chloro-2-(4-chloro-3,5-dimethyl-phenoxymethyl)-3-hydroxy-cyclopentyl]-hept-5-enoic acid;

(Z)-7-[(1R,2S,3R,5R)-5-Chloro-2-(4-chloro-naphthalen-1-yloxymethyl)-3-hydroxy-cyclopentyl]-hept-5-enoic acid;

(Z)-7-[(1R,2S,3R,5R)-5-Chloro-2-(3-chloro-2-fluoro-5-trifluoromethyl-phenoxymethyl)-3-hydroxy-cyclopentyl]-hept-5-enoic acid;

(Z)-7-[(1R,2S,3R,5R)-5-Chloro-2-(4-formyl-phenoxymethyl)-3-hydroxy-cyclopentyl]-hept-5-enoic acid;

(Z)-7-[(1R,2S,3R,5R)-5-Chloro-3-hydroxy-2-(4-hydroxymethyl-phenoxymethyl)-cyclopentyl]-hept-5-enoic acid;

(Z)-7-{(1R,2S,3R,5R)-5-Chloro-3-hydroxy-2-[4-(1-hydroxy-butyl)-phenoxymethyl]-cyclopentyl}-hept-5-enoic acid;

(Z)-7-{(1R,2S,3R,5R)-5-Chloro-3-hydroxy-2-[4-(1-methoxy-butyl)-phenoxymethyl]-cyclopentyl}-hept-5-enoic acid;

(Z)-7-{(1R,2S,3R,5R)-5-Chloro-3-hydroxy-2-[4-(1-hydroxy-hexyl)-phenoxymethyl]-cyclopentyl}-hept-5-enoic acid;

(Z)-7-{(1R,2S,3R,5R)-5-Chloro-3-hydroxy-2-[4-(1-hydroxy-ethyl)-phenoxymethyl]-cyclopentyl}-hept-5-enoic acid;

(Z)-7-[(1R,2S,3R,5R)-5-Chloro-2-(3-formyl-phenoxymethyl)-3-hydroxy-cyclopentyl]-hept-5-enoic acid;

(Z)-7-[(1R,2S,3R,5R)-5-Chloro-3-hydroxy-2-(3-hydroxymethyl-phenoxymethyl)-cyclopentyl]-hept-5-enoic acid;

(Z)-7-{(1R,2S,3R,5R)-5-Chloro-3-hydroxy-2-[3-(1-hydroxy-hexyl)-phenoxymethyl]-cyclopentyl}-hept-5-enoic acid;

(Z)-7-{(1R,2S,3R,5R)-5-Chloro-3-hydroxy-2-[3-(1-hydroxy-2-methyl-propyl)-phenoxymethyl]-cyclopentyl}-hept-5-enoic acid;

(Z)-7-{(1R,2S,3R,5R)-5-Chloro-3-hydroxy-2-[3-(1-hydroxy-butyl)-phenoxymethyl]-cyclopentyl}-hept-5-enoic acid;

(Z)-7-{(1R,2S,3R,5R)-5-Chloro-3-hydroxy-2-[3-(1-hydroxy-2-phenyl-ethyl)-phenoxymethyl]-cyclopentyl}-hept-5-enoic acid;

(Z)-7-{(1R,2S,3R,5R)-5-Chloro-3-hydroxy-2-[3-(1-hydroxy-ethyl)-phenoxymethyl]-cyclopentyl}-hept-5-enoic acid;

(Z)-7-[(1R,2S,3R,5R)-5-Chloro-3-hydroxy-2-(2-hydroxymethyl-phenoxymethyl)-cyclopentyl]-hept-5-enoic acid;

(Z)-7-[(1R,2S,3R,5R)-5-Chloro-3-hydroxy-2-(4-hydroxymethyl-3,5-dimethyl-phenoxymethyl)-cyclopentyl]-hept-5-enoic acid;

(Z)-7-[(1R,2S,3R,5R)-5-Chloro-3-hydroxy-2-(4-methoxymethyl-3,5-dimethyl-phenoxymethyl)-cyclopentyl]-hept-5-enoic acid;

(Z)-7-[(1R,2S,3R,5R)-5-Chloro-3-hydroxy-2-(1-oxo-indan-4-yloxymethyl)-cyclopentyl]-hept-5-enoic acid;

(Z)-7-[(1R,2S,3R,5R)-5-Chloro-3-hydroxy-2-(1-hydroxy-indan-4-yloxymethyl)-cyclopentyl]-hept-5-enoic acid;

(Z)-7-[(1R,2S,3R,5R)-5-Chloro-3-hydroxy-2-(5-hydroxy-5,6,7,8-tetrahydro-naphthalen-1-yloxymethyl)-cyclopentyl]-hept-5-enoic acid;

(Z)-7-{(1R,2S,3R,5R)-5-Chloro-3-hydroxy-2-[2-(2-hydroxy-ethyl)-phenoxymethyl]-cyclopentyl}-hept-5-enoic acid;

(Z)-7-{(1R,2S,3R,5R)-5-Chloro-3-hydroxy-2-[3-(2-hydroxy-ethyl)-phenoxymethyl]-cyclopentyl}-hept-5-enoic acid;

(Z)-7-{(1R,2S,3R,5R)-5-Chloro-3-hydroxy-2-[4-(2-hydroxy-ethyl)-phenoxymethyl]-cyclopentyl}-hept-5-enoic acid;

(Z)-7-[(1R,2S,3R,5R)-2-(3-Acetoxymethyl-5-chloro-phenoxymethyl)-5-chloro-3-hydroxy-cyclopentyl]-hept-5-enoic acid;

(Z)-7-[(1R,2S,3R,5R)-5-Chloro-2-(3-chloro-5-hydroxymethyl-phenoxymethyl)-3-hydroxy-cyclopentyl]-hept-5-enoic acid;

(Z)-7-{(1R,2S,3R,5R)-5-Chloro-3-hydroxy-2-[4-(2-hydroxy-ethyl)-3,5-dimethyl-phenoxymethyl]-cyclopentyl}-hept-5-enoic acid;

(Z)-7-[(1R,2S,3R,5R)-5-Chloro-2-(3,5-dichloro-phenoxymethyl)-3-hydroxy-cyclopentyl]-hept-5-enoic acid isopropyl ester;

(Z)-7-[(1R,2S,3R,5R)-5-Chloro-2-(3,5-dimethyl-phenoxymethyl)-3-hydroxy-cyclopentyl]-hept-5-enoic acid isopropyl ester;

(Z)-7-[(1R,2S,3R,5R)-2-(3,5-Bis-trifluoromethyl-phenoxymethyl)-5-chloro-3-hydroxy-cyclopentyl]-hept-5-enoic acid isopropyl ester;

(Z)-7-[(1R,2S,3R,5R)-5-Chloro-3-hydroxy-2-(3-trifluoromethyl-phenoxymethyl)-cyclopentyl]-hept-5-enoic acid isopropyl ester; and (Z)-7-[(1R,2S,3R,5R)-5-Chloro-3-hydroxy-2-(4-hydroxymethyl-phenoxymethyl)-cyclopentyl]-hept-5-enoic acid isopropyl ester.

In another embodiment, said compound, salt thereof, and/or prodrug thereof is used to treat and/or prevent glaucoma and/or ocular hypertension in a mammal.

In another embodiment, said compound, and/or salt thereof, and/or prodrug thereof is used in the manufacture of a medicament for the treatment and/or prevention of glaucoma and/or ocular hypertension in a mammal.

Another embodiment is a composition comprising said compound, and/or salt thereof, and/or prodrug thereof, wherein said composition is ophthalmically acceptable.

Use of this compound in the treatment and/or prevention, and/or in the manufacture of a medicament for the treatment and/or prevention, of any disease and/or condition mentioned herein as related to prostaglandin EP2 activity is also contemplated.

The compounds disclosed in Table 1 herein are useful for the prevention or treatment of glaucoma or ocular hypertension in mammals, or for the manufacture of a medicament for the treatment of glaucoma or ocular hypertension. They are also useful for the treatment of those diseases disclosed in the art as being amenable to treatment by prostaglandin $EP_2$ agonist, such as the ones listed previously.

Each compound of Table 1 is individually and specifically contemplated as an embodiment. Furthermore, pharmaceutically acceptable salts or prodrugs of the compounds of Table 1 are also contemplated as embodiments.

Each compound of Table 1 is individually and specifically contemplated for the treatment or prevention of glaucoma or ocular hypertension. Furthermore, use of pharmaceutically acceptable salts or prodrugs of the compounds of Table 1 is also contemplated.

Each compound of Table 1 is individually and specifically contemplated for use in the manufacture of a medicament for the treatment or prevention of glaucoma or ocular hypertension. Furthermore, use of pharmaceutically acceptable salts or prodrugs of the compounds of Table 1 is also contemplated.

Each compound of Table 1 is individually and specifically contemplated for use in the manufacture of a medicament for the treatment or prevention of glaucoma or ocular hypertension. Furthermore, use of pharmaceutically acceptable salts or prodrugs of the compounds of Table 1 is also contemplated.

A composition which is ophthalmically acceptable is individually and specifically contemplated for each compound of Table 1, and pharmaceutically acceptable salts thereof, and prodrugs thereof. Furthermore, use of pharmaceutically acceptable salts or prodrugs of the compounds of Table 1 is also contemplated.

The determination of whether a compound is active at a prostaglandin EP2 receptor is well within the ability of a person of ordinary skill in the art. While not intending to limit the scope of the invention in any way, one method of making such a determination is also provided in the examples herein.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient. The actual dose of the active compounds of the present invention depends on the specific compound, and on the condition to be treated; the selection of the appropriate dose is well within the knowledge of the skilled artisan.

The compounds disclosed herein are also useful in combination with other drugs useful for the treatment of glaucoma or other conditions.

For the treatment of glaucoma, combination treatment with the following classes of drugs is contemplated:

β-Blockers (or β-adrenergic antagonists) including carteolol, levobunolol, metiparanolol, timolol hemihydrate, timolol maleate, 1-selective antagonists such as betaxolol, and the like, or pharmaceutically acceptable salts or prodrugs thereof;

Adrenergic Agonists including non-selective adrenergic agonists such as epinephrine borate, epinephrine hydrochloride, and dipivefrin, and the like, or pharmaceutically acceptable salts or prodrugs thereof; and $\alpha_2$-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including direct acting cholinergic agonists such as charbachol, pilocarpine hydrochloride, pilocarbine nitrate, pilocarpine, and the like, or pharmaceutically acceptable salts or prodrugs thereof;

chlolinesterase inhibitors such as demecarium, echothiophate, physostigmine, and the like, or pharmaceutically acceptable salts or prodrugs thereof;

Glutamate Antagonists such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, bamidipine, verapamil, lidoflazine, prenylamine lactate, amiloride, and the like, or pharmaceutically acceptable salts or prodrugs thereof;

Prostamides such as bimatoprost, or pharmaceutically acceptable salts or prodrugs thereof; and Prostaglandins including travoprost, UFO-21, chloprostenol, fluprostenol, 13,14-dihydro-chloprostenol, latanoprost and the like.

TABLE 1

| Example | Structure | hEP2 flipr EC50 | hEP2 cAMP EC50 | hEP2 Ki | hEP4 flipr EC50 | hEP4 Ki | hFP | hEP1 | hEP3 | hTP | hIP | hDP |
| --- | --- | --- | --- | --- | --- | --- | --- | --- | --- | --- | --- | --- |
| 15 | (structure) | 11 | 8 | 8 | 12985 | 2294 | NA | NA | 2800 | NA | NA | 6228 |

TABLE 1-continued

| Example | Structure | hEP2 | | | hEP4 | | Other Receptors | | | | | |
|---|---|---|---|---|---|---|---|---|---|---|---|---|
| | | flipr EC50 | cAMP EC50 | Ki | flipr EC50 | Ki | hFP | hEP1 | hEP3 | hTP | hIP | hDP |
| 16 | | 100 | 40 | 45 | 13060 | 4111 | NA | NA | 1699 | NA | NA | NA |
| 17 | | 301 | 27 | 61 | 3424 | 507 | NA | NA | NA | NA | NA | NA |
| 18 | | 453 | 65 | 89 | 6311 | 973 | NA | NA | NA | NA | NA | NA |
| 19 | | 3 | 2 | 17 | 115 | 315 | NA | 2202 | 5867 | NA | NA | NA |
| 20 | | 82 | 28 | 163 | 2745 | 351 | NA | 7655 | | NA | NA | NA |
| 21 | | 26 | 37 | 303 | 449 | 5014 | NA | NA | | NA | NA | NA |
| 22 | | 18 | 5 | 43 | 823 | >10000 | >10000 | 10772 | | 6784 | NA | NA |
| 23 | | 45 | 10 | 32 | 2860 | 3223 | NA | 4889 | | NA | NA | NA |

TABLE 1-continued
| Example | Structure | hEP2 flipr EC50 | hEP2 cAMP EC50 | Ki | hEP4 flipr EC50 | Ki | Other Receptors hFP | hEP1 | hEP3 | hTP | hIP | hDP |
|---|---|---|---|---|---|---|---|---|---|---|---|---|
| 24 | 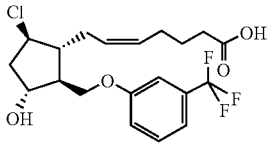 | 66 | 2.4 | 44 | 9870 | 1422 | NA | >10000 | 7428 | NA | 7280 | NA |
| 25 | 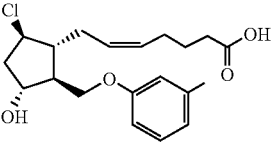 | 112 | 9 | 155 | 13026 | 1836 | NA | NA | NA | 13514 | 180 | NA |
| 26 | 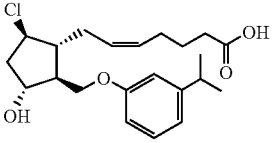 | 41 | 7 | 151 | 6496 | 967 | NA | 3018 | 100 | 342 | 43 | NA |
| 27 | 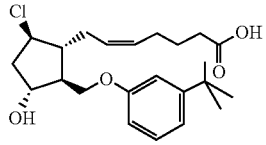 | 189 | 54 | 497 | 15973 | 908 | NA | 3257 | NA | NA | NA | NA |
| 28 | 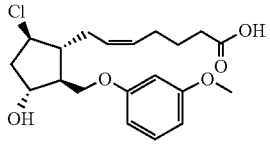 | 245 | 20 | 274 | 3719 | 1678 | NA | 4341 | 1718 | NA | NA | NA |
| 29 | 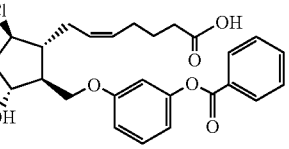 | 1580 | 139 | 568 | 7676 | 2385 | NA | 83 | 943 | NA | NA | NA |
| 30 | 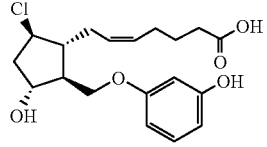 | 111 | 24 | 603 | 1173 | 5062 | NA | NA | NA | NA | NA | NA |
| 31 | 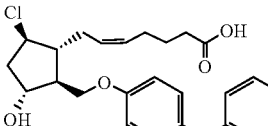 | >10000 | | >10000 | NA | 1741 | | | | | | |
| 32 | 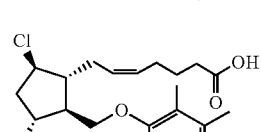 | 61 | 3 | 122 | >10000 | 1324 | NA | 572 | 1994 | 234 | 902 | NA |

TABLE 1-continued

| Example | Structure | hEP2 | | | hEP4 | | Other Receptors | | | | | |
|---|---|---|---|---|---|---|---|---|---|---|---|---|
| | | flipr EC50 | cAMP EC50 | Ki | flipr EC50 | Ki | hFP | hEP1 | hEP3 | hTP | hIP | hDP |
| 33 | | 277 | 72 | 620 | 7253 | | NA | 132 | 1262 | 948 | 437 | NA |
| 34 | | 51 | 2.4 | 172 | >10000 | 1105 | NA | 3380 | 387 | 1954 | 691 | NA |
| 35 | | 5578 | 3354 | 4324 | >10000 | >10000 | NA | 1770 | NA | 280 | 1103 | NA |
| 36 | | 27 | 1.4 | 31 | 7719 | 1090 | NA | NA | NA | NA | 3019 | NA |
| 37 | | 618 | 27 | 50 | >10000 | 1099 | NA | NA | NA | 366 | 922 | >10000 |
| 38 | | 2.3 | 1.5 | 25 | >10000 | 606 | NA | NA | NA | 1639 | 444 | 497 |
| 39 | | 10 | 0.7 | 11 | >10000 | 281 | NA | NA | NA | NA | NA | >10000 |
| 40 | | 29 | 0.7 | 2 | 5893 | 491 | NA | NA | NA | NA | NA | NA |

TABLE 1-continued

| Example | Structure | hEP2 flipr EC50 | hEP2 cAMP EC50 | hEP2 Ki | hEP4 flipr EC50 | hEP4 Ki | Other Receptors hFP | hEP1 | hEP3 | hTP | hIP | hDP |
|---|---|---|---|---|---|---|---|---|---|---|---|---|
| 41 | | 13 | 1.3 | 16 | >10000 | 1707 | NA | NA | NA | NA | NA | 2314 |
| 42 | | >10000 | 18 | 1498 | NA | >10000 | | | | | | |
| 43 | | 44 | 5 | 993 | NA | >10000 | NA | NA | NA | NA | NA | NA |
| 44 | | 1095 | 66 | 2726 | NA | >10000 | NA | NA | NA | NA | NA | NA |
| 45 | | 661 | 47 | 904 | NA | 5281 | NA | NA | NA | NA | NA | NA |
| 46 | | 531 | 119 | 2355 | NA | 2653 | NA | NA | 2283 | NA | >10000 | NA |
| 47 | | 1936 | 124 | 5289 | NA | >10000 | NA | NA | NA | NA | NA | NA |

TABLE 1-continued

| Example | Structure | hEP2 flipr EC50 | hEP2 cAMP EC50 | hEP2 Ki | hEP4 flipr EC50 | hEP4 Ki | Other Receptors hFP | hEP1 | hEP3 | hTP | hIP | hDP |
|---|---|---|---|---|---|---|---|---|---|---|---|---|
| 48 | 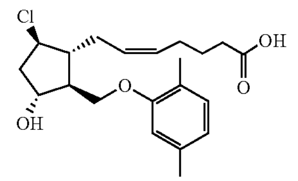 | 192 | 41 | 291 | >10000 | 14695 | NA | NA | NA | NA | 2694 | NA |
| 49 | 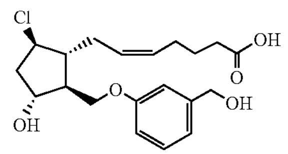 | 374 | 14 | 207 | NA | >10000 | NA | NA | NA | NA | >10000 | NA |
| 50 | 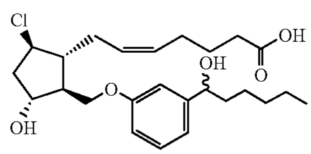 | 463 | 68 | 826 | NA | 1127 | NA | NA | 2865 | NA | NA | NA |
| 51 | 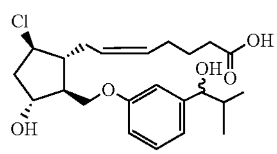 | 196 | 39 | 772 | NA | >10000 | NA | 4942 | 6706 | 5915 | 3506 | NA |
| 52 | 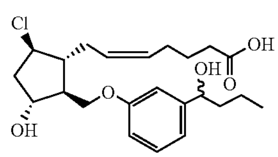 | 234 | 58 | 951 | >10000 | >10000 | NA | NA | 956 | NA | NA | NA |
| 53 | 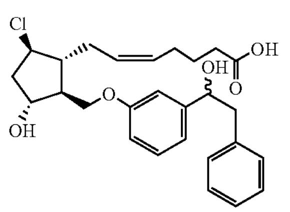 | 1734 | 496 | 1748 | NA | 1851 | NA | 2857 | NA | NA | NA | NA |
| 54 | 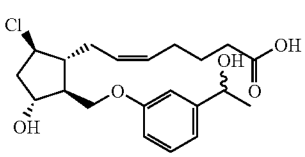 | 121 | 40 | 701 | NA | >10000 | NA | 1159 | 6270 | NA | NA | NA |
| 55 | 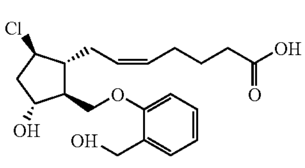 | 9495 | 225 | 4120 | 12308 | 1523 | NA | | 3833 | >10000 | | 3955 |

TABLE 1-continued

| Example | Structure | hEP2 flipr EC50 | hEP2 cAMP EC50 | hEP2 Ki | hEP4 flipr EC50 | hEP4 Ki | Other Receptors hFP | hEP1 | hEP3 | hTP | hIP | hDP |
|---|---|---|---|---|---|---|---|---|---|---|---|---|
| 56 | | 27 | 1.8 | 64 | NA | 2198 | NA | NA | 5762 | 365 | 400 | 4293 |
| 57 | | 142 | 23 | 195 | NA | 1661 | NA | NA | NA | NA | NA | NA |
| 58 | | 51 | 6.5 | 129 | NA | 2831 | NA | 774 | 544 | NA | NA | NA |
| 59 | | 108 | 1.2 | 139 | NA | 3003 | NA | 968 | 246 | 919 | 405 | >10000 |
| 60 | | 17 | 1 | 86 | 6974 | 1440 | NA | 2425 | 211 | 383 | 182 | NA |
| 61 | | 5977 | 128 | 3906 | >10000 | | NA | NA | 5320 | 427 | 137 | NA |
| 62 | | 1971 | 18 | 161 | >10000 | | NA | 2891 | 1899 | NA | NA | NA |

TABLE 1-continued

| Example | Structure | hEP2 flipr EC50 | hEP2 cAMP EC50 | hEP2 cAMP Ki | hEP4 flipr EC50 | hEP4 Ki | Other Receptors hFP | Other Receptors hEP1 | Other Receptors hEP3 | Other Receptors hTP | Other Receptors hIP | Other Receptors hDP |
|---|---|---|---|---|---|---|---|---|---|---|---|---|
| 63 | (structure) | >10000 | ND | 1987 | >10000 | | NA | 2067 | 660 | NA | NA | NA |
| 64 | (structure) | 1110 | 6.5 | 65 | 7448 | 381 | NA | | 833 | >10000 | NA | >10000 |
| 65 | (structure) | 520 | 2 | 64 | 10632 | 497 | NA | | 3925 | >10000 | NA | >10000 |
| 66 | (structure) | | | | | | | | | | | |

EXAMPLE 1

(Z)-7-((1R,5S)-2-Oxo-5-phenoxymethyl-cyclopent-3-enyl)-hept-5-enoic acid methyl ester (6a, FIG. 1)

Step 1: Mitsonobu Reaction of Phenol and 1 to Give 2a.

A solution of diisopropyl azodicarboxylate (DIAD, 194 μL, 1.0 mmol) in THF (1.5 mL) was added to a solution of alcohol 1 (441 mg, 1.0 mmol), triphenylphosphine (262 mg, 1.0 mmol) and phenol (94 mg, 1.0 mmol) in THF (3.0 mL). After stirring 18 h at room temperature, the solvent was removed under a stream of nitrogen and the residue was suspended in $Et_2O$ (50 mL). The mixture was washed with saturated aqueous $NaHCO_3$ (3×20 mL) and brine (20 mL) then the organic phase was dried ($Na_2SO_4$) filtered and concentrated in vacuo. Purification of the residue by flash column chromatography on silica gel (hexane→50% EtOAc/hexane, gradient) afforded 218 mg of the desired ether 2a contaminated with phenol (approximately 15% phenol by $^1H$ NMR analysis) which was taken on without further purification.

Step 2: Deprotection of 2a to Give 3a.

Pyridinium p-toluenesulfonate (PPTs, 9 mg, 0.036 mmol) was added to a solution of impure 2a (218 mg, ~0.36 mmol) in methanol (3.6 mL) at room temperature under nitrogen. The solution was heated at 50° C. for 4 h, then cooled and concentrated in vacuo. Purification of the crude residue by flash column chromatography on silica gel (60% EtOAc/hexane→EtOAc, gradient) afforded 112 mg (32% over two steps) of diol 3a.

Step 3: Silylation of 3a to Give 4a.

Triethylamine (67 μL, 0.48 mmol), dimethylaminopyridine (8 mg, 0.065 mmol), and tert-butyldimethylsilyl chloride (54 mg, 0.36 mmol) were sequentially added to a solution of 3a (112 mg, 0.32 mmol) in $CH_2Cl_2$ (1.6 mL). The resulting solution was stirred at room temperature under nitrogen for 18 h. The reaction mixture was then concentrated in vacuo, then saturated aqueous $NH_4Cl$ (20 mL) was added and the mixture was extracted with EtOAc (3×30 mL). The combined organic extracts were washed with brine (20 mL), dried ($Na_2SO_4$), filtered and concentrated in vacuo. Purification of the crude residue by flash column chromatography on silica gel (25%→60% EtOAc/hexane→EtOAc, gradient) afforded 96 mg (65%) of desired product 4a.

Step 4: Oxidation of 4a to Give 5a.

4-Methylmorpholine N-oxide (17.5 mg, 0.15 mmol) and 4 Å molecular sieves (25 mg) were added to a solution of 4a (46 mg, 0.10 mmol) in $CH_2Cl_2$ (0.5 mL). The mixture was cooled to 0° C. and tetrapropylammonium perruthenate (TPAP, 1.8 mg, 0.005 mmol) was added in one portion. The reaction mixture was allowed to warm to room temperature. After 18 h at room temperature the reaction was concentrated in vacuo. Purification of the crude residue by flash column chromatography on silica gel (15%→60% EtOAc/hexane) afforded 27 mg (59%) of 5a and 6 mg (18%) of the title compound (6a).

EXAMPLE 2

(Z)-7-((1R,2S,3R)-3-Hydroxy-5-oxo-2-phenoxymethyl-cyclopentyl)-hept-5-enoic acid methyl ester (7a, FIG. 1)

HF-pyridine (100 μL) was added to a solution of 5a (27 mg, 0.059 mmol) in $CH_3CN$ (1.2 mL) in a plastic scintillation vial at room temperature. After 18 h, the reaction was quenched with saturated aqueous $NaHCO_3$ (10 mL) and extracted with EtOAc (3×15 mL). The combined organic extracts were dried ($Na_2SO_4$), filtered and concentrated in vacuo. Purification of the crude residue by flash column chromatography on silica gel (40% EtOAc/hexane) afforded 9 mg (44%) of the title compound (7a) and 4 mg (21%) of 6a.

EXAMPLE 3 AND EXAMPLE 4

(Z)-7-((1R,5S)-2-Oxo-5-phenoxymethyl-cyclopent-3-enyl)-hept-5-enoic acid (8a) and (Z)-7-((1R,2S,3R)-3-Hydroxy-5-oxo-2-phenoxymethyl-cyclopentyl)-hept-5-enoic acid (9a)

Rabbit liver esterase (134 units/mg, 1 mg) was added to a solution of 6a (5.0 mg, 0.022 mmol) in MeCN (0.1 mL) and pH 7.2 buffer (0.72 mL). After stirring at room temperature for 18 h, the reaction mixture was diluted with MeCN (5 mL) and concentrated to dryness. The residue was suspended in $CH_2Cl_2$, filtered through celite and concentrated. Purification of the resulting crude residue by flash column chromatography on silica gel (70% EtOAc/hexane→EtOAc→2% MeOH/EtOAc, gradient) afforded 0.9 mg (20%) of title compound 8a and 3.0 mg (63%) of title compound 9a.

EXAMPLE 5

Figure 2:
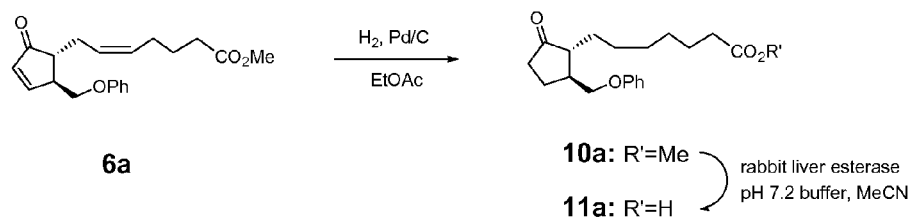
FIG. 2 depicts an exemplary method of preparing certain compounds disclosed herein.

7-((1R,5S)-2-Oxo-5-phenoxymethyl-cyclopentyl)-heptanoic acid methyl ester (10a, FIG. 2)

Palladium on carbon (10 wt. %, 3 mg) was added to a solution of 6a (9.0 mg, 0.027 mmol) in EtOAc (0.65 mL). A hydrogen atmosphere was established by evacuating and refilling with hydrogen (3×) and the reaction mixture was stirred under a balloon of hydrogen for 18 h. The reaction mixture was filtered through celite, washing with EtOAc, and the filtrate was concentrated in vacuo to afford 7.5 mg (82%) of the title compound (10a).

EXAMPLE 6

7-((1R,5S)-2-Oxo-5-phenoxymethyl-cyclopentyl)-heptanoic acid (11a, FIG. 2)

The product of example 5 (10a, 6.5 mg, 0.020 mmol) was converted to the title compound (11a, 4.0 mg (64%)) in accordance with the procedure in Examples 3 and 4.

EXAMPLE 7

Figure 3:
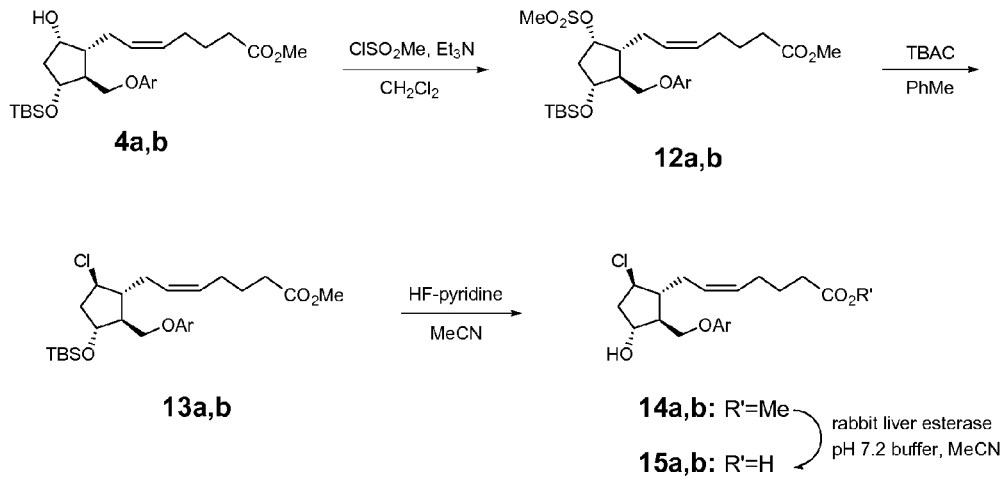
FIG. 3 depicts an exemplary method of preparing certain compounds disclosed herein.

(Z)-7-((1R,2S,3R,5R)-5-Chloro-3-hydroxy-2-phenoxymethyl-cyclopentyl)-hept-5-enoic acid methyl ester (14a, FIG. 3)

Step 1: Mesylation of 4a to Give 12a.
Triethylamine (23 μL, 0.17 mmol) and methanesulfonyl chloride (11 μL, 0.14 mmol) were added sequentially to a solution of 4a (51 mg, 0.11 mmol) in $CH_2Cl_2$ (0.8 mL) at room temperature. After 18 h at room temperature, saturated aqueous $NaHCO_3$ (5 mL) was added and the mixture was extracted with EtOAc (3×10 mL). The combined organic extracts were dried ($Na_2SO_4$), filtered and concentrated in vacuo. Purification of the crude residue by flash column chromatography on silica gel (25% EtOAc/hexane) afforded 47 mg (79%) of 12a.

Step 2: Conversion of 12a to Chloride 13a.
Tetrabutylammonium chloride (250 mg, 0.90 mmol) was added to a solution of 12a (47 mg, 0.087 mmol) in toluene (2.9 mL). The reaction mixture was heated at 50° C. for 18 h. The cooled mixture was diluted with brine (10 mL) and extracted with EtOAc (3×25 mL). The combined organic extracts were dried ($Na_2SO_4$), filtered and concentrated in vacuo. Purification of the crude residue by flash column chromatography on silica gel (15% EtOAc/hexane) afforded 32 mg (77%) of 13a.

Step 3. Deprotection of 13a to Give 14a.
HF-pyridine (100 μL) was added to a solution of 13a (27 mg, 0.059 mmol) in $CH_3CN$ (1.3 mL) in a plastic scintillation vial at room temperature. After 18 h, the reaction was quenched with saturated aqueous $NaHCO_3$ (10 mL) and extracted with EtOAc (3×15 mL). The combined organic extracts were dried ($Na_2SO_4$), filtered and concentrated in vacuo. Purification of the crude residue by flash column chromatography on silica gel (25% EtOAc/hexane) afforded 20 mg (82%) of the title compound (14a).

EXAMPLE 8

(Z)-7-((1R,2S,3R,5R)-5-Chloro-3-hydroxy-2-phenoxymethyl-cyclopentyl)-hept-5-enoic acid (15a, FIG. 3)

The product of example 7 (14a, 6.0 mg, 0.020 mmol) was converted to the title compound (15a, 2.5 mg (44%)) in accordance with the procedure in Examples 3 and 4.

EXAMPLE 9

Figure 4:
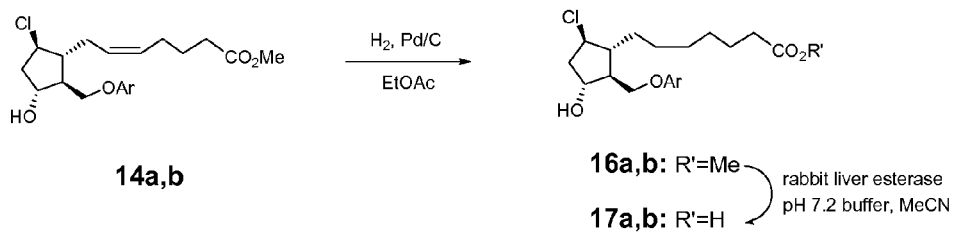
FIG. 4 depicts an exemplary method of preparing certain compounds disclosed herein.

7-((1R,2S,3R,5R)-5-Chloro-3-hydroxy-2-phenoxymethyl-cyclopentyl)-heptanoic acid methyl ester (16a, FIG. 4)

Palladium on carbon (10 wt. %, 3 mg) was added to a solution of 14a (9.0 mg, 0.027 mmol) in EtOAc (0.7 mL). A hydrogen atmosphere was established by evacuating and refilling with hydrogen (5×) and the reaction mixture was stirred under a balloon of hydrogen for 18 h. The reaction mixture was filtered through celite, washing with EtOAc, and the filtrate was concentrated in vacuo to afford 9.0 mg (quant.) of the title compound (16a).

EXAMPLE 10

7-((1R,2S,3R,5R)-5-Chloro-3-hydroxy-2-phenoxymethyl-cyclopentyl)-heptanoic acid (17a, FIG. 4)

The product of example 9 (16a, 8.0 mg, 0.021 mmol) was converted to the title compound (17a, 2.0 mg (26%)) in accordance with the procedure in Examples 3 and 4.

EXAMPLE 11

(Z)-7-[(1R,2S,3R,5R)-5-Chloro-2-(3,5-dichloro-phenoxymethyl)-3-hydroxy-cyclopentyl]-hept-5-enoic acid methyl ester (14a, FIG. 3 [see also FIG. 1])

Step 1: Mitsonobu Reaction of 3,5-dichlorophenol and 1 to Give 2b.
Diisopropyl azodicarboxylate (DIAD, 342 μL, 1.76 mmol) was added to a solution of alcohol 1 (676 mg, 1.53 mmol), triphenylphosphine (613 mg, 2.34 mmol) and 3,5-dichlorophenol (281 mg, 1.72 mmol) in THF (7.6 mL). After stirring 64 h at room temperature, the solvent was removed under a stream of nitrogen. The residue was diluted with EtOAc (75 mL) and then washed with saturated aqueous $NaHCO_3$ (3×30 mL) and brine (30 mL) then the organic phase was dried ($Na_2SO_4$) filtered and concentrated in vacuo. Purification of the residue by flash column chromatography on silica gel (15% EtOAc/hexane) afforded 627 mg of the desired ether 2b contaminated with 3,5-dichlorophenol (approximately 14% phenol by $^1H$ NMR analysis) which was taken on without further purification.

Step 2: Deprotection of 2b to Give 3b.

Pyridinium p-toluenesulfonate (PPTs, 23 mg, 0.092 mmol) was added to a solution of impure 2b (627 mg, ~0.92 mmol) in methanol (9.2 mL) at room temperature under nitrogen. The solution was heated at 50° C. for 16 h, then cooled and concentrated in vacuo. Purification of the crude residue by flash column chromatography on silica gel (65% EtOAc/hexane→EtOAc, gradient) afforded 220 mg (34% over two steps) of diol 3b.

Step 3: Silylation of 3b to Give 4b.

Triethylamine (110 µL, 0.79 mmol), dimethylaminopyridine (13 mg, 0.11 mmol), and tert-butyldimethylsilyl chloride (88 mg, 0.58 mmol) were sequentially added to a solution of 3b (220 mg, 0.53 mmol) in $CH_2Cl_2$ (2.6 mL). The resulting solution was stirred at room temperature under nitrogen for 18 h. The reaction mixture was then concentrated under a stream of nitrogen, then saturated aqueous $NH_4Cl$ (30 mL) was added and the mixture was extracted with EtOAc (3×50 mL). The combined organic extracts were washed with brine (25 mL), dried ($Na_2SO_4$), filtered and concentrated in vacuo. Purification of the crude residue by flash column chromatography on silica gel (15%→70% EtOAc/hexane→EtOAc, gradient) afforded 163 mg (58%) of 4b.

Step 4: Mesylation of 4b to Give 12b.

Triethylamine (31 µL, 0.22 mmol) and methanesulfonyl chloride (15 µL, 0.19 mmol) were added sequentially to a solution of 4b (80 mg, 0.15 mmol) in $CH_2Cl_2$ (1.1 mL) at room temperature. After 18 h at room temperature, saturated aqueous $NaHCO_3$ (10 mL) was added and the mixture was extracted with EtOAc (3×20 mL). The combined organic extracts were dried ($Na_2SO_4$), filtered and concentrated in vacuo. Purification of the crude residue by flash column chromatography on silica gel (15% EtOAc/hexane) afforded 53 mg (58%) of 12b.

Step 5: Conversion of 12b to Chloride 13b and 14b.

Tetrabutylammonium chloride (250 mg, 0.90 mmol) was added to a solution of 12b (53 mg, 0.087 mmol) in toluene (2.9 mL). The reaction mixture was heated at 50° C. for 18 h. The cooled mixture was diluted with brine (10 mL) and extracted with EtOAc (3×25 mL). The combined organic extracts were dried ($Na_2SO_4$), filtered and concentrated in vacuo. Purification of the crude residue by flash column chromatography on silica gel (10%→50% EtOAc/hexane, gradient) afforded 33 mg (69%) of 13b and 10 mg (26%) of the title compound (14b).

Step 6. Deprotection of 13b to Give 14b.

HF-pyridine (100 µL) was added to a solution of 13a (33 mg, 0.060 mmol) in $CH_3CN$ (1.2 mL) in a plastic scintillation vial at room temperature. After 18 h, the reaction was quenched with saturated aqueous $NaHCO_3$ (10 mL) and extracted with EtOAc (3×15 mL). The combined organic extracts were dried ($Na_2SO_4$), filtered and concentrated in vacuo. Purification of the crude residue by flash column chromatography on silica gel (25% EtOAc/hexane) afforded 25 mg (96%) of the title compound (14b).

EXAMPLE 12

(Z)-7-[(1R,2S,3R,5R)-5-Chloro-2-(3,5-dichlorophenoxymethyl)-3-hydroxy-cyclopentyl]-hept-5-enoic acid (15b, FIG. 3)

The product of example 11 (14b, 10 mg, 0.023 mmol) was converted to the title compound (15b, 3.0 mg (31%)) in accordance with the procedure in Examples 3 and 4.

EXAMPLE 13

7-[(1R,2S,3R,5R)-5-Chloro-2-(3,5-dichloro-phenoxymethyl)-3-hydroxy-cyclopentyl]-heptanoic acid methyl ester (16b, FIG. 4)

Palladium on carbon (10 wt. %, 3 mg) was added to a solution of 14b (9.0 mg, 0.027 mmol) in EtOAc (0.5 mL). A hydrogen atmosphere was established by evacuating and refilling with hydrogen (5×) and the reaction mixture was stirred under a balloon of hydrogen for 18 h. The reaction mixture was filtered through celite, washing with EtOAc, and the filtrate was concentrated in vacuo. Purification of the crude residue by flash column chromatography on silica gel (15% EtOAc/hexane) afforded 2.5 mg (28%) of the title compound (16b).

EXAMPLE 14

7-[(1R,2S,3R,5R)-5-Chloro-2-(3,5-dichloro-phenoxymethyl)-3-hydroxy-cyclopentyl]-heptanoic acid (17b, FIG. 4)

The product of example 13 (16b, 2.0 mg, 0.005 mmol) was converted to the title compound (17b, 0.6 mg (31%)) in accordance with the procedure in Examples 3 and 4.

Preparation 1

Figure 5:
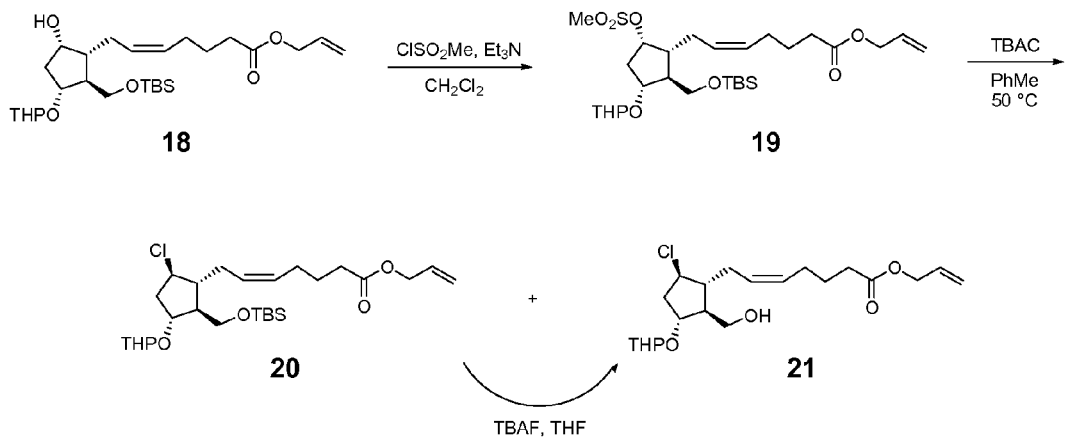
FIG. 5 depicts an exemplary method of preparing synthetic intermediates to certain compounds disclosed herein.

(Z)-7-[(1R,2S,3R,5R)-5-Chloro-2-hydroxymethyl-3-(tetrahydro-pyran-2-yloxy)-cyclopentyl]-hept-5-enoic acid allyl ester (21, FIG. 5)

Step 1: Mesylation of 18 to Give 19

Triethylamine (4.2 mL, 30 mmol) and methanesulfonyl chloride (1.9 mL, 24 mmol) were added sequentially to a solution of (Z)-7-[(1R,2S,3R,5S)-2-(tert-butyl-dimethyl-silanyloxymethyl)-5-hydroxy-3-(tetrahydro-pyran-2-yloxy)-cyclopentyl]-hept-5-enoic acid allyl ester (18, 9.94 g, 20 mmol) in $CH_2Cl_2$ (150 mL) at 0° C. The reaction mixture was allowed to warm to rt. After 18 h at rt, the reaction mixture was added to saturated aqueous $NaHCO_3$ (200 mL) and $CH_2Cl_2$ was removed in vacuo. The resulting aqueous mixture was extracted with EtOAc (3×300 mL). The combined extracts were washed with brine (100 mL), dried ($Na_2SO_4$), filtered and concentrated in vacuo to afford 11.5 g (quant.) of mesylate 19 as a pale yellow oil.

Step 2: Conversion of 19 to Chlorides 20 and 21

A mixture of 19 (1.73 g, 3.01 mmol) and tetrabutylammonium chloride (8.4 g, 30.2 mmol) in toluene (100 mL) was stirred at 50° C. After 18 h, the reaction was cooled to rt and brine (150 mL) was added. The mixture was extracted with EtOAc (3×200 mL). The combined extracts were washed with brine (150 mL), dried (Na$_2$SO$_4$), filtered and concentrated in vacuo. Purification of the crude residue by flash column chromatography on silica gel (10%→25%→50% EtOAc/hexane, gradient) afforded 695 mg (45%) of chloride 20 along with 223 mg (18%) of the title compound (21).

Step 3: Deprotection of 20 to Give 21

Tetrabutylammonium fluoride (4.0 mL of a 1.0 M THF solution, 4.0 mmol) was added to a solution of 20 (695 mg, 1.35 mmol) in THF (5.4 mL) at 0° C. under N$_2$. The reaction mixture was allowed to warm to rt. After 18 h at rt, THF was removed under a stream of N$_2$. EtOAc (100 mL) was added and the resulting mixture was washed with H$_2$O (2×50 mL) and brine (50 mL) then dried (Na$_2$SO$_4$), filtered and concentrated in vacuo. Purification of the crude residue by flash column chromatography on silica gel (30% EtOAc/hexane) afforded 392 mg (72%) of the title compound (21) as a colorless oil.

EXAMPLE 15

Figure 6:
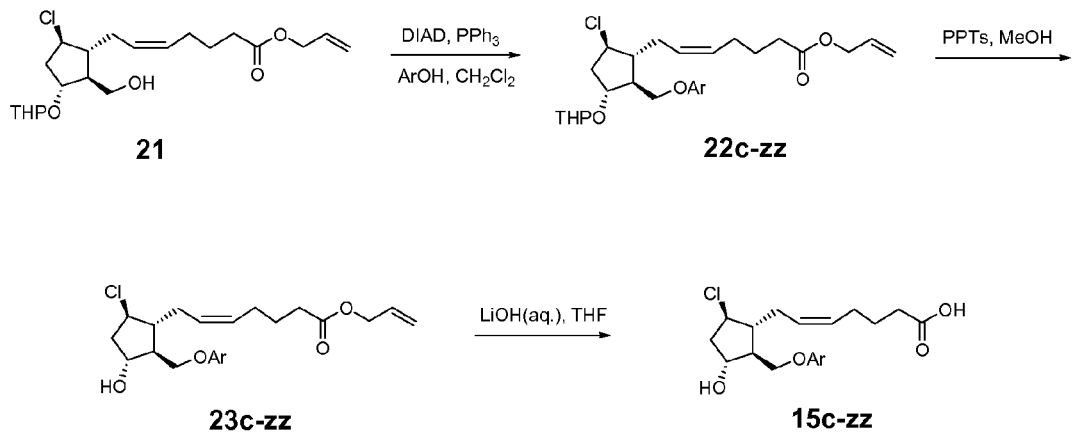
FIG. 6 depicts an exemplary method of preparing certain compounds disclosed herein.

(Z)-7-[(1R,2S,3R,5R)-2-(3,5-Bis-trifluoromethyl-phenoxymethyl)-5-chloro-3-hydroxy-cyclopentyl]-hept-5-enoic acid (15c, FIG. 6)

Step 1: Mitsunobu Reaction of 21 and Hydroxyaryl to Give 22c.

DIAD (50 µL, 0.26 mmol) was added to a solution of alcohol 21 (88 mg, 0.22 mmol), triphenylphosphine (88 mg, 0.34 mmol) and 3,5-bis(trifluoromethyl)phenol (40 µL, 0.26 mmol) in CH$_2$Cl$_2$ (1.1 mL). After stirring overnight at rt, the solvent was removed under a stream of nitrogen. The residue was diluted with EtOAc (25 mL), washed with saturated aqueous NaHCO$_3$ (3×10 mL) and brine (10 mL) then the organic phase was dried (Na$_2$SO$_4$) filtered and concentrated in vacuo. Purification of the residue by flash column chromatography on silica gel (10% EtOAc/hexane) afforded 112 mg (83%) of the desired ether 22c.

Step 2: Deprotection of 22c to Give 23c.

Pyridinium p-toluenesulfonate (PPTs, 5 mg, 0.019 mmol) was added to a solution of 22c (112 mg, 0.18 mmol) in methanol (1.8 mL) at rt under nitrogen. The solution was heated at 50° C. overnight, then cooled and concentrated in vacuo. Purification of the crude residue by flash column chromatography on silica gel (25% EtOAc/hexane→EtOAc, gradient) afforded 24 mg (25%) of pure 22c and 67 mg (70%) of 22c contaminated with ~10% of a slightly more polar impurity.

Step 3: Saponification of 22c to Give 15c.

Lithium hydroxide (0.05 mL of a 1.0 M aqueous solution, 0.05 mmol) was added to a solution of ester 22c (9 mg, 0.017 mmol) in THF (0.17 mL). After stirring overnight at rt, the solvent was removed under a stream of nitrogen. H$_2$O (2 mL) was added, the mixture was acidified with 1.0 M aqueous HCl (0.5 mL), and the resulting cloudy solution was extracted with EtOAc (3×10 mL). The combined extracts were washed with brine (10 mL), dried (Na$_2$SO$_4$), filtered and concentrated in vacuo to afford 8 mg (96%) of the title compound (15c).

EXAMPLE 16

Figure 7:
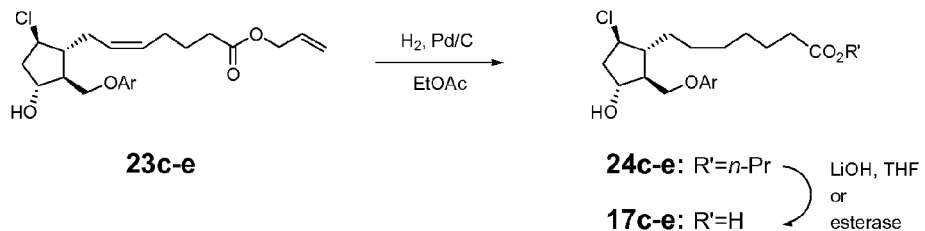
FIG. 7 depicts an exemplary method of preparing certain compounds disclosed herein.

(Z)-7-[(1R,2S,3R,5R)-2-(3,5-Bis-trifluoromethyl-phenoxymethyl)-5-chloro-3-hydroxy-cyclopentyl]-heptanoic acid (17c, FIG. 7)

Step 1: Hydrogenation of 23c to Give 24c.

Palladium on carbon (10 wt. %, 3 mg) was added to a solution of 23c (12 mg, 0.023 mmol) in EtOAc (0.5 mL). A hydrogen atmosphere was established by evacuating and refilling with hydrogen (5×) and the reaction mixture was stirred under a balloon of hydrogen for 4 h. The reaction mixture was filtered through celite, washing with EtOAc, and the filtrate was concentrated in vacuo to afford 12 mg (99%) of propyl ester 24c.

Step 2: Saponification of 24c to Give 17c.

Lithium hydroxide (0.1 mL of a 1.0 M aqueous solution, 0.1 mmol) was added to a solution of ester 24c (10 mg, 0.019 mmol) in THF (0.19 mL). The mixture was heated at 40° C. for 3 h, then cooled and the solvent was removed under a stream of nitrogen. H$_2$O (2 mL) was added, the mixture was acidified with 1.0 M aqueous HC; (0.5 mL), and the resulting cloudy solution was extracted with EtOAc (3×10 mL). The combined extracts were washed with brine (10 mL), dried (Na$_2$SO$_4$), filtered and concentrated in vacuo. Purification of the crude residue by flash column chromatography on silica gel (25%→50% EtOAc/hexane, gradient) afforded 8.5 mg (85%) starting material 24c and 1.3 mg (14%) of the title compound (17c).

EXAMPLE 17

(Z)-7-[(1R,2S,3R,5R)-5-Chloro-3-hydroxy-2-(naphthalen-2-yloxymethyl)-cyclopentyl]-hept-5-enoic acid (15d)

Alcohol 21 (86 mg, 0.21 mmol) and 2-naphthol (37 mg, 0.26 mmol) were converted into the title compound (15d) in accordance with the procedures of Example 15.

EXAMPLE 18

(Z)-7-[(1R,2S,3R,5R)-5-Chloro-3-hydroxy-2-(naphthalen-2-yloxymethyl)-cyclopentyl]-heptanoic acid (17d)

Step 1: Hydrogenation of 23d to Give 24d.

Alkene 23d from Example 17, step 2 (21 mg, 0.047 mmol) was converted into 20 mg (94%) of propyl ester 24d in accordance with step 1 of Example 16.

Step 2: Esterase Reaction of 24d to Give 17d.

Propyl ester 24d (19 mg, 0.043 mmol) was converted into 2 mg (12%) the title compound (17d) in accordance with the procedure in Examples 3 and 4; 8 mg (42%) of the starting ester (24d) was also recovered.

EXAMPLE 19

(Z)-7-[(1R,2S,3R,5R)-5-Chloro-3-hydroxy-2-(naphthalen-1-yloxymethyl)-cyclopentyl]-hept-5-enoic acid (15e)

Alcohol 21 (51 mg, 0.13 mmol) and 1-naphthol (22 mg, 0.15 mmol) were converted into the title compound (15e) in accordance with the procedures of Example 15.

EXAMPLE 20

(Z)-7-[(1R,2S,3R,5R)-5-Chloro-3-hydroxy-2-(naphthalen-1-yloxymethyl)-cyclopentyl]-heptanoic acid (17e)

Alkene 23e from Example 19, step 2 (16 mg, 0.036 mmol) was converted into the title compound (17e) in accordance with the procedures in Example 16; the second step was carried out at 40° C. for 20 h.

EXAMPLE 21

(Z)-7-[(1R,2S,3R,5R)-5-Chloro-2-(2-chloro-phenoxymethyl)-3-hydroxy-cyclopentyl]-hept-5-enoic acid (15f)

Alcohol 21 (78 mg, 0.20 mmol) and 2-chlorophenol (23 μL, 0.23 mmol) were converted into the title compound (15f) in accordance with the procedures of Example 15.

EXAMPLE 22

(Z)-7-[(1R,2S,3R,5R)-5-Chloro-2-(3-chloro-phenoxymethyl)-3-hydroxy-cyclopentyl]-hept-5-enoic acid (15 g)

Alcohol 21 (78 mg, 0.20 mmol) and 3-chlorophenol (24 μL, 0.23 mmol) were converted into the title compound (15 g) in accordance with the procedures of Example 15.

EXAMPLE 23

(Z)-7-[(1R,2S,3R,5R)-5-Chloro-2-(4-chloro-phenoxymethyl)-3-hydroxy-cyclopentyl]-hept-5-enoic acid (15h)

Alcohol 21 (78 mg, 0.20 mmol) and 4-chlorophenol (29 mg, 0.23 mmol) were converted into the title compound (15h) in accordance with the procedures of Example 15.

EXAMPLE 24

(Z)-7-[(1R,2S,3R,5R)-5-Chloro-3-hydroxy-2-(3-trifluoromethyl-phenoxymethyl)-cyclopentyl]-hept-5-enoic acid (15i)

Alcohol 21 (100 mg, 0.25 mmol) and 3-trifluoromethylphenol (36 μL, 0.30 mmol) were converted into the title compound (15i) in accordance with the procedures of Example 15.

EXAMPLE 25

(Z)-7-((1R,2S,3R,5R)-5-Chloro-3-hydroxy-2-m-tolyloxymethyl-cyclopentyl)-hept-5-enoic acid (15j)

Alcohol 21 (109 mg, 0.27 mmol) and m-cresol (36 μL, 0.33 mmol) were converted into the title compound (15j) in accordance with the procedures of Example 15.

EXAMPLE 26

(Z)-7-[(1R,2S,3R,5R)-5-Chloro-3-hydroxy-2-(3-isopropyl-phenoxymethyl)-cyclopentyl]-hept-5-enoic acid (15k)

Alcohol 21 (105 mg, 0.26 mmol) and 3-isopropylphenol (43 μL, 0.31 mmol) were converted into the title compound (15k) in accordance with the procedures of Example 15.

EXAMPLE 27

(Z)-7-[(1R,2S,3R,5R)-2-(3-tert-Butyl-phenoxymethyl)-5-chloro-3-hydroxy-cyclopentyl]-hept-5-enoic acid (15l)

Alcohol 21 (121 mg, 0.30 mmol) and 3-tert-butylphenol (54 mg, 0.36 mmol) were converted into the title compound (15l) in accordance with the procedures of Example 15.

EXAMPLE 28

(Z)-7-[(1R,2S,3R,5R)-5-Chloro-3-hydroxy-2-(3-methoxy-phenoxymethyl)-cyclopentyl]-hept-5-enoic acid (15m)

Alcohol 21 (104 mg, 0.26 mmol) and 3-methoxyphenol (34 μL, 0.31 mmol) were converted into the title compound (15m) in accordance with the procedures of Example 15.

EXAMPLE 29

Figure 8:
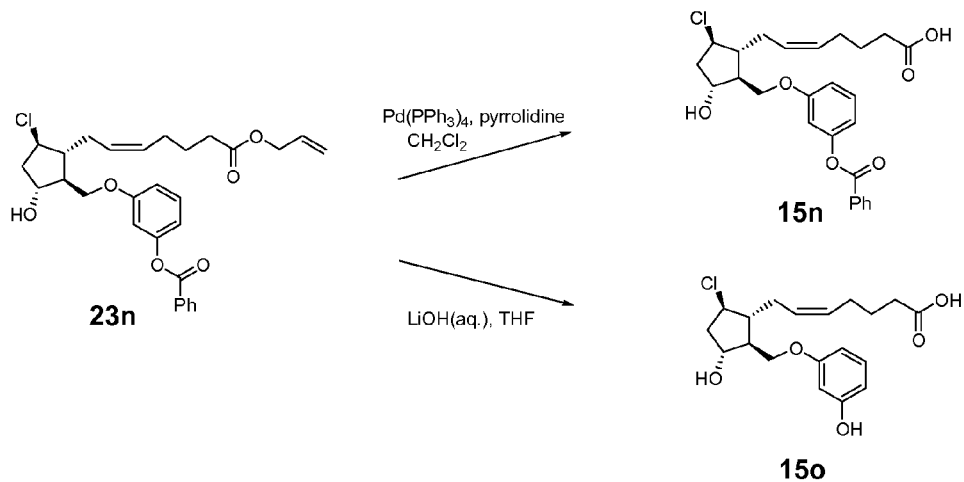
FIG. 8 depicts an exemplary method of preparing certain compounds disclosed herein.

3-[(1S,2R,3R,5R)-2-((Z)-6-carboxy-hex-2-enyl)-3-chloro-5-hydroxy-cyclopentylmethoxy]-phenyl benzoate (15n, FIG. 8)

Step 1 and 2: Mitsunobu Reaction and THP Deprotection to Give 23n.

Alcohol 21 (70 mg, 0.18 mmol) and monobenzoyl resorcinol (43 mg, 0.20 mmol) were converted into benzoate 23n in accordance with the procedures of Example 15, steps 1 and 2.

Step 3: Deallylation of 23n to Give 15n.

Tetrakis(triphenylphosphine)palladium(0) (2 mg, 0.0017 mmol) was added to a solution of allyl ester 23n (17.5 mg, 0.034 mmol) in $CH_2Cl_2$ (0.34 mL). The reaction mixture was cooled to 0° C. and pyrrolidine (3.1 mL, 0.037 mmol) was added. After 15 min at 0° C. the solvent was removed under a stream of nitrogen. $H_2O$ (2 mL) and 1.0 M aqueous HCl (1 mL) were added and the mixture was extracted with EtOAc (3×10 mL). The combined extracts were washed with brine (10 mL), dried ($Na_2SO_4$), filtered and concentrated in vacuo. Purification of the crude residue by flash column chromatography on silica gel (60%→80% EtOAc/hexane→EtOAc→10% MeOH/EtOAc, gradient) afforded 1.7 mg (11%) of the title compound (15n).

EXAMPLE 30

(Z)-7-[(1R,2S,3R,5R)-5-Chloro-3-hydroxy-2-(3-hydroxy-phenoxymethyl)-cyclopentyl]-hept-5-enoic acid (15o, FIG. 8)

Ester 23n from Example 29, step 2 was converted to the title compound (15o) in accordance with the procedure of Example 15, step 3.

EXAMPLE 31

(Z)-7-{(1R,2S,3R,5R)-5-Chloro-3-hydroxy-2-[4-(1-methyl-1-phenyl-ethyl)-phenoxymethyl]-cyclopentyl}-hept-5-enoic acid (15p)

Alcohol 21 (130 mg, 0.32 mmol) and 4-cumylphenol (83 mg, 0.39 mmol) were converted into the title compound (15p) in accordance with the procedures of Example 15.

EXAMPLE 32

(Z)-7-[(1R,2S,3R,5R)-5-Chloro-2-(2,3-dimethyl-phenoxymethyl)-3-hydroxy-cyclopentyl]-hept-5-enoic acid (15q)

Alcohol 21 (153 mg, 0.38 mmol) and 2,3-dimethylphenol (56 mg, 0.46 mmol) were converted into the title compound (15q) in accordance with the procedures of Example 15.

EXAMPLE 33

(Z)-7-[(1R,2S,3R,5R)-5-Chloro-2-(2,4-dimethyl-phenoxymethyl)-3-hydroxy-cyclopentyl]-hept-5-enoic acid (15r)

Alcohol 21 (117 mg, 0.29 mmol) and 2,4-dimethylphenol (42 μL, 0.35 mmol) were converted into the title compound (15r) in accordance with the procedures of Example 15.

EXAMPLE 34

(Z)-7-[(1R,2S,3R,5R)-5-Chloro-2-(2,5-dimethyl-phenoxymethyl)-3-hydroxy-cyclopentyl]-hept-5-enoic acid (15s)

Alcohol 21 (118 mg, 0.29 mmol) and 2,5-dimethylphenol (43 mg, 0.35 mmol) were converted into the title compound (15s) in accordance with the procedures of Example 15.

EXAMPLE 35

(Z)-7-[(1R,2S,3R,5R)-5-Chloro-2-(2,6-dimethyl-phenoxymethyl)-3-hydroxy-cyclopentyl]-hept-5-enoic acid (15t)

Alcohol 21 (131 mg, 0.33 mmol) and 2,6-dimethyl phenol (50 mg, 0.41 mmol) were converted into the title compound (15t) in accordance with the procedures of Example 15.

EXAMPLE 36

(Z)-7-[(1R,2S,3R,5R)-5-Chloro-2-(3,5-dimethyl-phenoxymethyl)-3-hydroxy-cyclopentyl]-hept-5-enoic acid (15u)

Alcohol 21 (112 mg, 0.28 mmol) and 3,5-dimethylphenol (41 mg, 0.34 mmol) were converted into the title compound (15u) in accordance with the procedures of Example 15.

EXAMPLE 37

(Z)-7-[(1R,2S,3R,5R)-5-Chloro-2-(3,4-dimethyl-phenoxymethyl)-3-hydroxy-cyclopentyl]-hept-5-enoic acid (15v)

Alcohol 21 (150 mg, 0.37 mmol) and 3,4-dimethylphenol (55 mg, 0.45 mmol) were converted into the title compound (15v) in accordance with the procedures of Example 15.

EXAMPLE 38

(Z)-7-[(1R,2S,3R,5R)-5-Chloro-3-hydroxy-2-(3,4,5-trimethyl-phenoxymethyl)-cyclopentyl]-hept-5-enoic acid (15w)

Alcohol 21 (70 mg, 0.18 mmol) and 3,4,5-trimethylphenol (28 mg, 0.21 mmol) were converted into the title compound (15w) in accordance with the procedures of Example 15.

EXAMPLE 39

(Z)-7-[(1R,2S,3R,5R)-5-Chloro-2-(4-chloro-3,5-dimethyl-phenoxymethyl)-3-hydroxy-cyclopentyl]-hept-5-enoic acid (15x)

Alcohol 21 (33 mg, 0.082 mmol) and 4-chloro-3,5-dimethylphenol (15 mg, 0.096 mmol) were converted into the title compound (15x) in accordance with the procedures of Example 15.

EXAMPLE 40

(Z)-7-[(1R,2S,3R,5R)-5-Chloro-2-(4-chloro-naphthalen-1-yloxymethyl)-3-hydroxy-cyclopentyl]-hept-5-enoic acid (15y)

Alcohol 21 (78 mg, 0.20 mmol) and 4-chloro-1-naphthnol (40 mg, 0.22 mmol) were converted into the title compound (15y) in accordance with the procedures of Example 15.

EXAMPLE 41

(Z)-7-[(1R,2S,3R,5R)-5-Chloro-2-(3-chloro-2-fluoro-5-trifluoromethyl-phenoxymethyl)-3-hydroxy-cyclopentyl]-hept-5-enoic acid (15z)

Alcohol 21 (78 mg, 0.20 mmol) and 3-chloro-2-fluoro-5-trifluoromethylphenol (49 mg, 0.23 mmol) were converted into the title compound (15z) in accordance with the procedures of Example 15.

EXAMPLE 42

(Z)-7-[(1R,2S,3R,5R)-5-Chloro-2-(4-formyl-phenoxymethyl)-3-hydroxy-cyclopentyl]-hept-5-enoic acid (15aa)

Alcohol 21 (155 mg, 0.39 mmol) and 4-hydroxybenzaldehyde (55 mg, 0.45 mmol) were converted into the title compound (15aa) in accordance with the procedures of Example 15.

EXAMPLE 43

Figure 9:
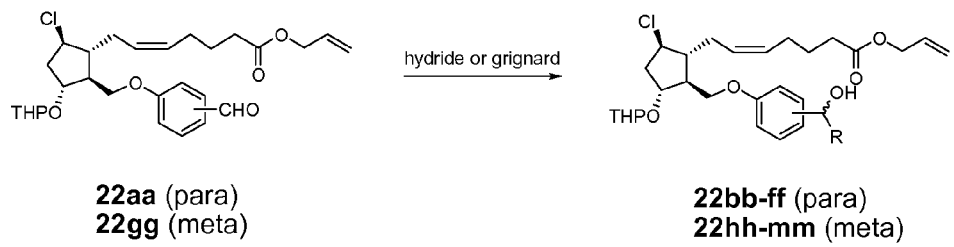
FIG. 9 depicts an exemplary method of preparing certain compounds disclosed herein.

(Z)-7-[(1R,2S,3R,5R)-5-Chloro-3-hydroxy-2-(4-hydroxymethyl-phenoxymethyl)-cyclopentyl]-hept-5-enoic acid (15bb, FIG. 9)

Step 1: Reduction of Aldehyde 22aa to Alcohol 22bb

Sodium borohydride (1.8 mg, 0.048 mmol) and methanol (0.05 mL) were added sequentially to a solution of aldehyde 22aa from Example 42, step 1 (25 mg, 0.048 mmol) at 0° C. After 5 min at 0° C., the reaction was quenched by addition of 1.0 M aqueous HCl (0.5 mL). The mixture was diluted with $H_2O$ and extracted with EtOAc (3×10 mL). The combined extracts were dried ($Na_2SO_4$), filtered and concentrated in vacuo. Purification of the crude residue by flash column chromatography on silica gel (30% EtOAc/hexane) afforded 15 mg (60%) of alcohol 22bb.

Step 2: Deprotection of 22bb to Give 23bb

Alcohol 22bb (15 mg, 0.030 mmol) was converted into 10 mg (80%) of diol 23bb in accordance with the procedure of Example 15, step 2.

Step 3: Saponification of 23bb to Give 15bb.

Diol ester 23bb (10 mg, 0.024 mmol) was converted into 9 mg (99%) of the title compound (15bb) in accordance with the procedure of Example 15, step 3.

EXAMPLE 44

Figure 10:
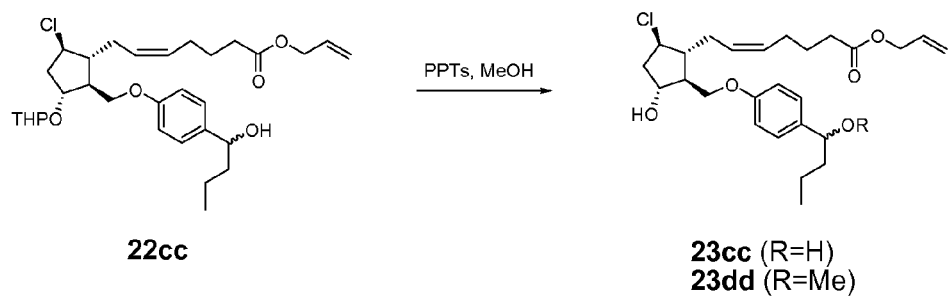
FIG. 10 depicts an exemplary method of preparing certain compounds disclosed herein.

(Z)-7-{(1R,2S,3R,5R)-5-Chloro-3-hydroxy-2-[4-(1-hydroxy-butyl)-phenoxymethyl]-cyclopentyl}-hept-5-enoic acid (15cc, FIGS. 9 and 10)

Step 1: Grignard Addition to Aldehyde 22aa n-Propylmagnesium chloride (2.0 M solution in $Et_2O$, 30 μL, 0.06 mmol) was added to a solution of aldehyde 22aa from Example 42, step 1 (30 mg, 0.059 mmol) in THF (0.3 mL) at 0° C. under nitrogen. After 2 h at 0° C., the reaction was quenched by the addition of saturated aqueous NH$_4$Cl (5 mL) and THF was removed under a stream of nitrogen. The resulting mixture was extracted with EtOAc (3×15 mL). The combined extracts were washed with brine (10 mL), dried (Na$_2$SO$_4$), filtered and concentrated in vacuo to afford 32 mg (98%) of alcohol 22cc.

Step 2: Deprotection of 22cc to give 23cc and 23dd

Ether 22cc (32 mg, 0.058 mmol) was converted to 4 mg (15%) of diol 23cc and 20 mg (72%) of methyl ether 23dd in accordance with the procedure of Example 15, step 2.

Step 3: Saponification of 23cc to Give 15cc

Ester 23cc (4 mg, 0.009 mmol) was converted into 3 mg (82%) of the title compound (15cc) in accordance with the procedure of Example 15, step 3.

EXAMPLE 45

(Z)-7-{(1R,2S,3R,5R)-5-Chloro-3-hydroxy-2-[4-(1-methoxy-butyl)-phenoxymethyl]-cyclopentyl}-hept-5-enoic acid (15dd, FIGS. 9 and 10)

Ester 23dd from Example 44, step 2 (10 mg, 0.021 mmol) was converted into 8.5 mg (92%) of the title compound (15dd) in accordance with the procedure of Example 15, step 3.

EXAMPLE 46

Figure 11:
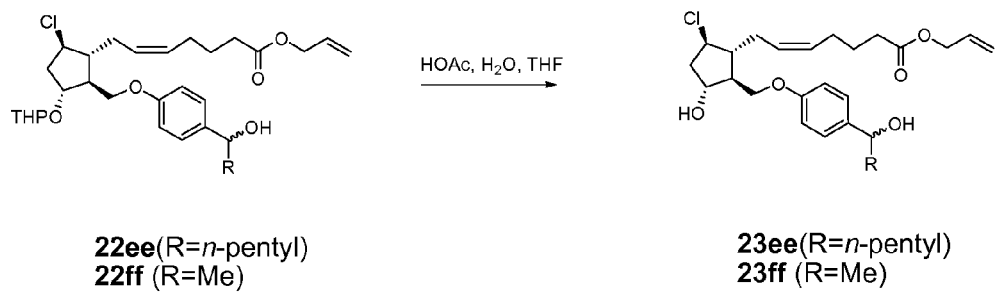
FIG. 11 depicts an exemplary method of preparing certain compounds disclosed herein.

(Z)-7-{(1R,2S,3R,5R)-5-Chloro-3-hydroxy-2-[4-(1-hydroxy-hexyl)-phenoxymethyl]-cyclopentyl}-hept-5-enoic acid (15ee, FIGS. 9 and 11)

Step 1: Grignard Addition to Aldehyde 22aa

Addition of pentylmagnesium bromide (2.0 M in Et$_2$O, 20 µL, 0.04 mmol) to aldehyde 22aa from Example 42, step 1 (19 mg, 0.038 mmol) was carried out in accordance with the procedure of Example 44, step 1 to afford 5 mg (23%) of alcohol 22ee.

Step 2: Deprotection of Alcohol 22ee to Give Diol 23ee

A mixture of acetic acid, THF and H$_2$O (4:2:1, 0.2 mL) was added to alcohol 22ee (5 mg, 0.009 mmol) and the resulting mixture was heated at 40° C. overnight. After 18 h, the reaction was allowed to cool to rt then toluene (5 mL) was added and the mixture was concentrated in vacuo. Purification of the crude residue by flash column chromatography on silica gel (35% EtOAc/hexane) afforded 2 mg (47%) of diol 23ee.

Step 3: Saponification of 23ee to Give 15ee

Ester 23ee (3 mg, 0.004 mmol) was converted into 1.8 mg (98%) of the title compound (15ee) in accordance with the procedure of Example 15, step 3.

EXAMPLE 47

(Z)-7-{(1R,2S,3R,5R)-5-Chloro-3-hydroxy-2-[4-(1-hydroxy-ethyl)-phenoxymethyl]-cyclopentyl}-hept-5-enoic acid (15ff, FIGS. 9 and 11)

Methylmagnesium bromide (3.0 M in Et$_2$O, 20 µL, 0.06 mmol) and aldehyde 22aa from Example 42, step 1 (22 mg, 0.044 mmol) were converted into the title compound (15ff) in accordance with the procedures of Example 46.

EXAMPLE 48

(Z)-7-[(1R,2S,3R,5R)-5-Chloro-2-(3-formyl-phenoxymethyl)-3-hydroxy-cyclopentyl]-hept-5-enoic acid (15gg)

Alcohol 21 (206 mg, 0.51 mmol) and 3-hydroxybenzaldehyde (73 mg, 0.60 mmol) were converted into the title compound (15gg) in accordance with the procedures of Example 15.

EXAMPLE 49

(Z)-7-[(1R,2S,3R,5R)-5-Chloro-3-hydroxy-2-(3-hydroxymethyl-phenoxymethyl)-cyclopentyl]-hept-5-enoic acid (15hh, FIG. 9)

Aldehyde 22gg from Example 48, step 1 was converted to the title compound (15hh) in accordance with the procedures of Example 43.

EXAMPLE 50

(Z)-7-{(1R,2S,3R,5R)-5-Chloro-3-hydroxy-2-[3-(1-hydroxy-hexyl)-phenoxymethyl]-cyclopentyl}-hept-5-enoic acid (15ii, FIG. 9)

Step 1: Grignard Addition to Aldehyde 22gg

Addition of pentylmagnesium bromide (2.0 M in Et$_2$O, 32 µL, 0.064 mmol) to aldehyde 22gg from Example 48, step 1 (16 mg, 0.032 mmol) was carried out in accordance with the procedure of Example 44, step 1 to afford 17 mg (100%) of alcohol 22ii.

Step 2: Deprotection of Alcohol 22ii to Give Diol 23ii.

Ether 22ii (17 mg, 0.032 mmol) was converted to 11 mg (70%) of diol 23ii in accordance with the procedure of Example 15, step 2.

Step 3: Saponification of 23ii to give 15ii

Ester 23ii (11 mg, 0.022 mmol) was converted into 9 mg (89%) of the title compound (15ii) in accordance with the procedure of Example 15, step 3.

EXAMPLE 51

(Z)-7-{(1R,2S,3R,5R)-5-Chloro-3-hydroxy-2-[3-(1-hydroxy-2-methyl-propyl)-phenoxymethyl]-cyclopentyl}-hept-5-enoic acid (15jj, FIG. 9)

Isopropylmagnesium chloride (2.0 M in Et$_2$O, 30 µL, 0.06 mmol) and aldehyde 22gg from Example 48, step 1 (15.5 mg, 0.031 mmol) were converted into the title compound (15jj) in accordance with the procedures of Example 50.

EXAMPLE 52

(Z)-7-{(1R,2S,3R,5R)-5-Chloro-3-hydroxy-2-[3-(1-hydroxy-butyl)-phenoxymethyl]-cyclopentyl}-hept-5-enoic acid (15kk, FIG. 9)

n-Propylmagnesium chloride (2.0 M in Et$_2$O, 30 µL, 0.06 mmol) and aldehyde 22gg from Example 48, step 1 (15.7 mg, 0.031 mmol) were converted into the title compound (15kk) in accordance with the procedures of Example 50.

EXAMPLE 53

(Z)-7-{(1R,2S,3R,5R)-5-Chloro-3-hydroxy-2-[3-(1-hydroxy-2-phenyl-ethyl)-phenoxymethyl]-cyclopentyl}-hept-5-enoic acid (15ll, FIG. 9)

Benzylmagnesium chloride (2.0 M in THF, 35 μL, 0.07 mmol) and aldehyde 22gg from Example 48, step 1 (17.5 mg, 0.035 mmol) were converted into the title compound (15ll) in accordance with the procedures of Example 50.

EXAMPLE 54

(Z)-7-{(1R,2S,3R,5R)-5-Chloro-3-hydroxy-2-[3-(1-hydroxy-ethyl)-phenoxymethyl]-cyclopentyl}-hept-5-enoic acid (15 mm, FIG. 9)

Methylmagnesium bromide (3.0 M in Et$_2$O, 21 μL, 0.063 mmol) and aldehyde 22gg from Example 48, step 1 (15.7 mg, 0.031 mmol) were converted into the title compound (15 mm) in accordance with the procedures of Example 50.

EXAMPLE 55

(Z)-7-[(1R,2S,3R,5R)-5-Chloro-3-hydroxy-2-(2-hydroxymethyl-phenoxymethyl)-cyclopentyl]-hept-5-enoic acid (15nn)

Alcohol 21 (150 mg, 0.37 mmol) and 2-(tert-butyldimethylsilanyloxymethyl)-phenol (see Ankala, S. V. and Fenteany, G., *Tetrahedron Lett.* 2002, 43, 4729-4732, 104 mg, 0.43 mmol) were converted into the title compound (15nn) in accordance with the procedures of Example 15.

EXAMPLE 56

(Z)-7-[(1R,2S,3R,5R)-5-Chloro-3-hydroxy-2-(4-hydroxymethyl-3,5-dimethyl-phenoxymethyl)-cyclopentyl]-hept-5-enoic acid (15 pp)

Step 1: Alcohol 21 (73 mg, 0.18 mmol) and 2,6-dimethyl-4-hydroxybenzaldehyde (32 mg, 0.21 mmol) were converted into 53 mg (54%) of aldehyde 22oo in accordance with the procedure of Example 15, step 1.

Step 2: Aldehyde 22oo (53 mg, 0.10 mmol) was converted into 53 mg (quant.) of alcohol 22 pp in accordance with the procedure of Example 43, step 1.

Step 3: Alcohol 22 pp (24 mg, 0.045 mmol) was converted into 5 mg (52%) of diol 23 pp in accordance with the procedure of Example 46, step 2.

Step 4: Ester 23 pp (10 mg, 0.022 mmol) was converted into 5 mg (53%) of the title compound (15 pp) in accordance with the procedure of Example 15, step 3.

EXAMPLE 57

(Z)-7-[(1R,2S,3R,5R)-5-Chloro-3-hydroxy-2-(4-methoxymethyl-3,5-dimethyl-phenoxymethyl)-cyclopentyl]-hept-5-enoic acid (15qq)

Step 1: Alcohol 22 pp from Example 56, step 2 (22 mg, 0.041 mmol) was converted into 10 mg (52%) of methyl ether 23qq xx in accordance with the procedure of Example 15, step 2.

Step 2: Ester 23qq (10 mg, 0.022 mmol) was converted into 5 mg (53%) of the title compound (15qq) in accordance with the procedure of Example 15, step 3.

EXAMPLE 58

(Z)-7-[(1R,2S,3R,5R)-5-Chloro-3-hydroxy-2-(1-oxo-indan-4-yloxymethyl)-cyclopentyl]-hept-5-enoic acid (15rr)

Alcohol 21 (100 mg, 0.25 mmol) and 4-hydroxyindanone (43 mg, 0.29 mmol) were converted into the title compound (15rr) in accordance with the procedures of Example 15.

EXAMPLE 59

(Z)-7-[(1R,2S,3R,5R)-5-Chloro-3-hydroxy-2-(1-hydroxy-indan-4-yloxymethyl)-cyclopentyl]-hept-5-enoic acid (15ss)

Step 1: Ketone 22rr from example 58, step 1 (55 mg, 0.10 mmol) was converted into 11 mg (20%) of alcohol 22ss in accordance with the procedure of Example 43, step 1; the reaction was carried out for 30 min, and 35 mg (64%) of the starting ketone 22rr was also isolated.

Step 2: Ether 22ss (11 mg, 0.021 mmol) was converted into 5 mg (54%) of diol 23ss in accordance with the procedure of Example 15, step 2.

Step 3: Ester 23ss (5 mg, 0.01 mmol) was converted into 4 mg (88%) of the title compound (15ss) in accordance with the procedure of Example 15, step 3.

EXAMPLE 60

(Z)-7-[(1R,2S,3R,5R)-5-Chloro-3-hydroxy-2-(5-hydroxy-5,6,7,8-tetrahydro-naphthalen-1-yloxymethyl)-cyclopentyl]-hept-5-enoic acid (15tt)

Alcohol 21 (127 mg, 0.32 mmol) and 5-hydroxy-1-tetralone (62 mg, 0.38 mmol) were converted into the title compound (15tt) in accordance with the procedures of Example 15 and Example 43, step 1; the reduction step was carried out after PPTs hydrolysis and before ester saponification.

EXAMPLE 61

(Z)-7-{(1R,2S,3R,5R)-5-Chloro-3-hydroxy-2-[2-(2-hydroxy-ethyl)-phenoxymethyl]-cyclopentyl}-hept-5-enoic acid (15uu)

Figure 12:
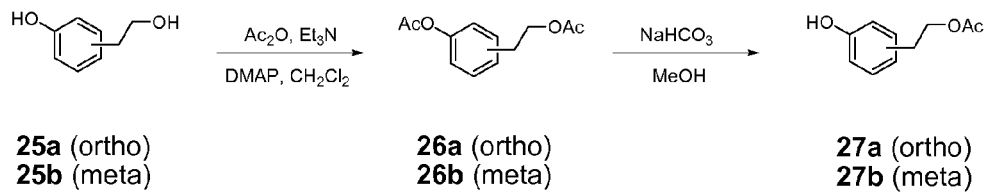
FIG. 12 depicts an exemplary method of preparing synthetic intermediates to certain compounds disclosed herein.

Step 1: Bis-acylation of hydroxyphenol 25a to Give 26a (FIG. 12).

Triethylamine (0.63 mL, 4.5 mmol), dimethylaminopyridine (37 mg, 0.30 mmol) and acetic anhydride (0.43 mL, 4.5 mmol) were added sequentially to a solution of 2-hydroxyphenethyl alcohol (25a, 417 mg, 3.0 mmol) in CH$_2$Cl$_2$ (6 mL). After stirring at rt overnight, the reaction was quenched with saturated aqueous NaHCO$_3$ and extracted with EtOAc (3×). The combined extracts were washed with H$_2$O and brine, dried (Na$_2$SO$_4$), filtered and concentrated in vacuo. Purification of the crude residue by flash column chromatography on silica gel (30% EtOAc/hexane) afforded 355 mg (53%) of diacetate 26a.

Step 2: Mono-deacylation of 26a to Give 27a (FIG. 12).

Saturated aqueous NaHCO$_3$ (10 mL) was added to a solution of diacetate 26a (355 mg, 1.60 mmol) in MeOH (4 mL) and the mixture was stirred overnight. After 24 h, the reaction was diluted with H$_2$O and extracted with EtOAc (3×). Combined extracts were dried (MgSO$_4$), filtered and concentrated in vacuo. Purification of the crude residue by flash column chromatography on silica gel (35% EtOAc/hexane) afforded 90 mg (31%) of phenol 27a.

Steps 3-5: Alcohol 21 (166 mg, 0.41 mmol) and phenol 27a (90 mg, 0.50 mmol) were converted into the title compound (15uu) in accordance with the procedures of Example 15.

EXAMPLE 62

(Z)-7-{(1R,2S,3R,5R)-5-Chloro-3-hydroxy-2-[3-(2-hydroxy-ethyl)-phenoxymethyl]-cyclopentyl}-hept-5-enoic acid (15vv)

2-(3-Hydroxyphenyl)ethanol (25b) was converted into the title compound (15vv) in accordance with the procedures of Example 61

EXAMPLE 63

(Z)-7-{(1R,2S,3R,5R)-5-Chloro-3-hydroxy-2-[4-(2-hydroxy-ethyl)-phenoxymethyl]-cyclopentyl}-hept-5-enoic acid (15ww)

Alcohol 21 (140 mg, 0.035 mmol) and 2-(4-hydroxyphenyl)-ethyl acetate (see Procopiou et al. *J. Org. Chem.* 1998, 63, 2342-2347, 76 mg, 0.42 mmol) were converted into the title compound (15ww) in accordance with the procedures of Example 15.

Preparation 2

Figure 13:
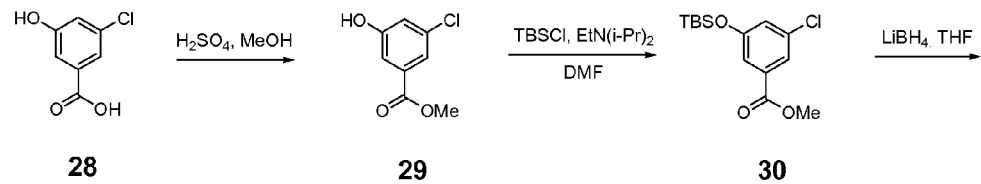
FIG. 13 depicts an exemplary method of preparing synthetic intermediates to certain compounds disclosed herein.
Figure 13:
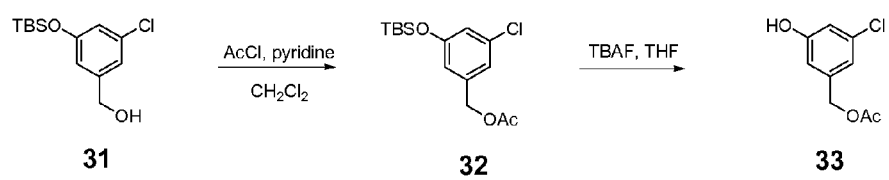

3-chloro-5-hydroxybenzyl acetate (33, FIG. 13)

Step 1: Methylation of 28 to Give 29.

Concentrated sulfuric acid (0.04 mL, 0.48 mmol) was added to a solution of 3-chloro-5-hydroxy-benzoic acid (28, 500 mg, 2.9 mmol) in MeOH (3.5 mL) and the resulting solution was heated at reflux for 5.5 h. The reaction was allowed to cool to rt then partitioned between saturated aqueous NaHCO$_3$ (50 mL) and EtOAc (50 mL). The phases were separated and the aqueous phase was extracted with EtOAc (2×20 mL). The combined organic phases were washed with brine (20 mL), dried (MgSO$_4$), filtered and concentrated in vacuo to afford 540 mg (99%) of ester 29.

Step 2: Silylation of 29 to Give 30.

Diisopropylethylamine (0.37 mL, 2.1 mmol) and tert-butyldimethylsilyl chloride (250 mg, 1.7 mmol) were added to a solution of phenol 29 (280 mg, 1.5 mmol) in DMF (1 mL) at 0° C. After 1 h, the reaction mixture was poured into EtOAc (50 mL) and H$_2$O (25 mL). The layers were separated and the organic phase was washed with H$_2$O (25 mL) and brine (20 mL), then dried (MgSO$_4$), filtered and concentrated in vacuo. Purification of the crude residue by flash column chromatography on silica gel (hexane→5% EtOAc/hexane) afforded 449 mg (99%) of silyl ether 30.

Step 3: Reduction of Ester 30 to Alcohol 31

A solution of ester 30 (220 mg, 0.73 mmol) in THF (1 mL) was added via syringe to a suspension of LiBH$_4$ (24 mg, 1.1 mmol) in THF (0.5 mL) at 0° C. The solution was heated at reflux. The reaction was cooled to rt and poured into a mixture of ice and 10% acetic acid. The mixture was extracted with EtOAc. The combined organic phase was washed with H$_2$O and brine then dried (MgSO$_4$), filtered and concentrated in vacuo. Purification of the crude residue by flash column chromatography on silica gel (10% EtOAc/hexane) afforded 149 mg (75%) of alcohol 31.

Step 4. Acylation of Alcohol 31 to Give Acetate 32.

Pyridine (49 µL, 0.61 mmol) and acetyl chloride (43 µl, 0.61 mmol) were added sequentially to a solution of alcohol 31 (150 mg, 0.55 mmol) in CH$_2$Cl$_2$ (1.0 mL). After 5 min, the reaction mixture was partitioned between saturated aqueous NaHCO$_3$ (10 mL) and CH$_2$Cl$_2$ (20 mL). The phases were separated and the aqueous phase was extracted with CH$_2$Cl$_2$ (2×15 mL). The combined organic phases were washed with brine (10 mL), dried (MgSO$_4$), filtered and concentrated in vacuo. Purification of the crude residue by flash column chromatography on silica gel (10% EtOAc/hexane) afforded 135 mg (78%) of acetate 32.

Step 5: Disilylation of 32 to Give Phenol 33.

Tetrabutylammonium fluoride (1.0 M in THF, 1.28 mL, 1.28 mmol) was added to a solution of silyl ether 32 (135 mg, 0.43 mmol) in THF (1.0 mL) and the reaction was allowed to stir overnight at rt. The reaction was then partitioned between H$_2$O (10 mL) and EtOAc (20 mL). The layers were separated and the organic phase was washed with H$_2$O (2×15 mL) and brine (10 mL), then dried (MgSO$_4$), filtered and concentrated in vacuo. Purification of the crude residue by flash column chromatography on silica gel (20% EtOAc/hexane) afforded 40 mg (56%) of the title compound (33).

EXAMPLE 64

Figure 14:
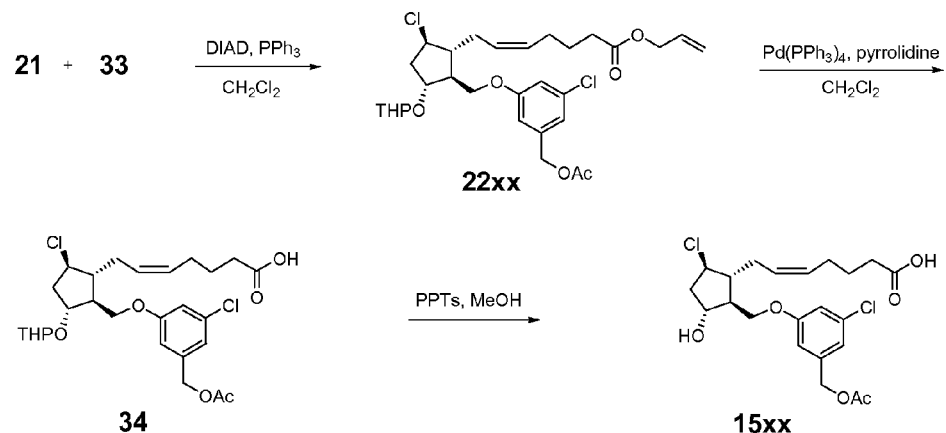
FIG. 14 depicts an exemplary method of preparing certain compounds disclosed herein.

(Z)-7-[(1R,2S,3R,5R)-2-(3-Acetoxymethyl-5-chloro-phenoxymethyl)-5-chloro-3-hydroxy-cyclopentyl]-hept-5-enoic acid (15xx, FIG. 14)

Step 1: Alcohol 21 (80 mg, 0.20 mmol) and phenol 33 from Preparation 2 (40 mg, 0.24 mmol) were converted into 70 mg (60%) of ether 22xx in accordance with the procedure of Example 15, step 1

Step 2: Ester 22xx (70 mg, 0.12 mmol) was converted into 60 mg (impure, contaminated with PPh$_3$) of acid 34 in accordance with the procedure of Example 29, step 3.

Step 3: Ether 34 (30 mg, 0.55 mmol) was converted into 5 mg (20%) of the title compound (15xx) in accordance with the procedure of Example 15, step 2

EXAMPLE 65

(Z)-7-[(1R,2S,3R,5R)-5-Chloro-2-(3-chloro-5-hydroxymethyl-phenoxymethyl)-3-hydroxy-cyclopentyl]-hept-5-enoic acid (15yy)

Acetate 15xx from Example 64 (1.7 mg, 0.037 mmol) was converted into 1.3 mg (84%) of the title compound (15yy) in accordance with the procedure of Example 15, step 3; the reaction time was 2 h.

Preparation 3

Figure 15:
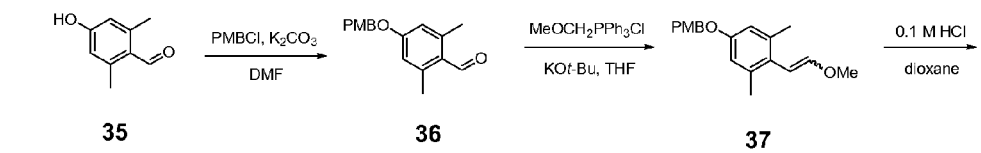
FIG. 15 depicts an exemplary method of preparing synthetic intermediates to certain compounds disclosed herein.
Figure 15:
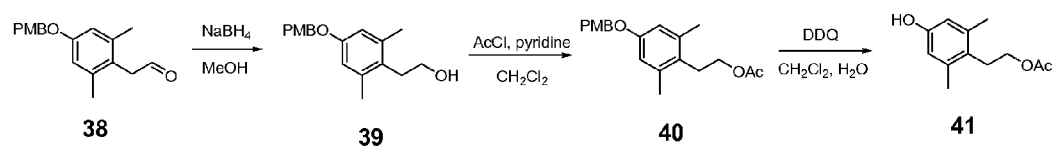

2-(4-hydroxy-2,6-dimethylphenyl)-ethyl acetate (41, FIG. 15)

Step 1: Protection of Phenol 35 to Give Aldehyde 36

A solution of 4-methoxybenzyl chloride (0.22 mL, 1.6 mmol) in DMF (2 mL) was added to a mixture of 4-hydroxy- 2,6-dimethylbenzaldehyde (35, 200 mg, 1.33 mmol) and $K_2CO_3$ (460 mg, 3.32 mmol) in DMF (8 mL). The mixture was heated at 100° C. for 2 h, then cooled to rt and partitioned between saturated aqueous $H_2O$ (25 mL) and EtOAc (40 mL). The phases were separated and the aqueous phase was extracted with EtOAc (40 mL). The combined organic phases were washed with $H_2O$ and brine, then dried ($MgSO_4$), filtered and concentrated in vacuo. Purification of the crude residue by flash column chromatography on silica gel (20% EtOAc/hexane) afforded 326 mg (91%) of 36.

Step 2: Wittig Reaction of 36 to Give Enol Ether 37.

Potassium tert-butoxide (104 mg, 0.93 mmol) was added to a solution of methoxymethyltriphenylphosphonium chloride (152 mg, 0.444 mmol) in THF (2 mL) at 0° C. After 30 min at 0° C., a solution of aldehyde 36 (100 mg, 0.37 mmol) in THF (1 mL) was added. The reaction mixture was allowed to warm to rt and stirred overnight. The reaction was quenched at 0° C. by the slow addition of $H_2O$ then was partitioned between 10% aqueous HCl (20 mL) and EtOAc (40 mL). The phases were separated and the aqueous phase was extracted with EtOAc (40 mL). The combined organic phases were washed with $H_2O$ and brine, then dried ($MgSO_4$), filtered and concentrated in vacuo. Purification of the crude residue by flash column chromatography on silica gel (20% EtOAc/hexane) afforded 83 mg (76%) of enol ether 37.

Step 3: Hydrolysis of Enol Ether 37 to Give Aldehyde 38

0.1 M aqueous HCl (90 μL, 0.09 mmol) was added to a solution of enol ether 37 (83 mg, 0.28 mmol) in dioxane (2.8 mL). After 1 h at rt, the mixture was heated at 60° C. for 2.5 h. The reaction mixture was partitioned between saturated aqueous $NaHCO_3$ (10 mL) and $CH_2Cl_2$ (10 mL). The phases were separated and the aqueous phase was extracted with $CH_2Cl_2$ (2×20 mL). The combined organic phases were washed with $H_2O$ and brine then dried ($MgSO_4$), filtered and concentrated in vacuo. Purification of the crude residue by flash column chromatography on silica gel (30% EtOAc/hexane) afforded 23 mg (29%) of aldehyde 38.

Step 4. Reduction of Aldehyde 38 to Alcohol 39.

Sodium borohydride (15 mg, 0.40 mmol) was added to a solution of aldehyde 38 (75 mg, 0.26 mmol) in MeOH (3.4 mL) at 0° C. The mixture was allowed to warm to rt. After 20 min at rt, the reaction was cooled to 0° C. and quenched by the slow addition of $H_2O$. The mixture was then diluted with $H_2O$ (20 mL) and extracted with EtOAc (2×35 mL). The combined organic phase was washed with brine, dried ($MgSO_4$), filtered and concentrated in vacuo. Purification of the crude residue by flash column chromatography on silica gel (50% EtOAc/hexane) afforded 63 mg (84%) of alcohol 39.

Step 5: Acylation of 39 to Give 40.

Alcohol 39 (63 mg, 0.22 mmol) was converted into 71 mg (99%) of acetate 40 in accordance with the procedure of Preparation 2, step 4.

Step 6: Deprotection of 40 to Give Phenol 41

2,3-Dichloro-5,6-dicyano-1,4-benzoquinone (DDQ, 23 mg, 0.10 mmol) was added to a mixture of ether 40 (30 mg, 0.091 mmol) in $CH_2Cl_2$ (0.9 mL) and $H_2O$ (47 μL) at 0° C. After 1 h at 0° C. the reaction was allowed to warm to rt. After 4 h at rt, the reaction was quenched with saturated aqueous $NaHCO_3$ (10 mL). The mixture was extracted with $CH_2Cl_2$ (3×10 mL). The combined extracts were washed with $H_2O$ and brine then dried ($MgSO_4$), filtered and concentrated in vacuo. Purification of the residue by flash column chromatography on silica gel (30% EtOAc/hexane) afforded 10 mg (53%) of the title compound (41).

EXAMPLE 66

(Z)-7-{(1R,2S,3R,5R)-5-Chloro-3-hydroxy-2-[4-(2-hydroxy-ethyl)-3,5-dimethyl-phenoxymethyl]-cyclopentyl}-hept-5-enoic acid (15zz)

Alcohol 21 (60 mg, 0.15 mmol) and phenol 41 from Preparation 3 (26 mg, 0.13 mmol) were converted into the title compound in accordance with the procedures of Example 15.

EXAMPLE 67

Figure 16:
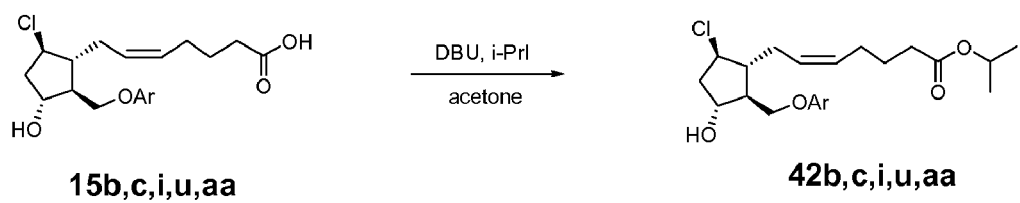
FIG. 16 depicts an exemplary method of preparing certain compounds disclosed herein.

(Z)-7-[(1R,2S,3R,5R)-5-Chloro-2-(3,5-dichloro-phenoxymethyl)-3-hydroxy-cyclopentyl]-hept-5-enoic acid isopropyl ester (42b, FIG. 16)

1,8-Diazabicyclo[5.4.0]undec-7-ene (7 μL, 0.05 mmol) was added to a solution of acid 15b from Example 12 (12.5 mg, 0.03 mmol) in acetone (0.3 mL) at rt. After 5 min, 2-iodopropane (15 μL, 0.15 mmol) was added. After 18 h at rt, the solvent was removed under a stream of nitrogen. The residue was diluted with EtOAc (15 mL) and washed with 1.0 M aqueous HCl (10 mL) and brine (10 mL) then dried ($Na_2SO_4$), filtered and concentrated in vacuo. Purification of the residue by flash column chromatography on silica gel (25% EtOAc/hexane→EtOAc, gradient) afforded 10 mg (73%) of the title compound (42b) along with 2.5 mg (20%) of recovered starting material 15b.

EXAMPLE 68

(Z)-7-[(1R,2S,3R,5R)-2-(3,5-Bis-trifluoromethyl-phenoxymethyl)-5-chloro-3-hydroxy-cyclopentyl]-hept-5-enoic acid isopropyl ester (42c)

Acid 15c from Example 15 (7 mg, 0.14 mmol) was converted into 7 mg (92%) of the title compound (42c) in accordance with the procedure of Example 67.

EXAMPLE 69

(Z)-7-[(1R,2S,3R,5R)-5-Chloro-3-hydroxy-2-(3-trifluoromethyl-phenoxymethyl)-cyclopentyl]-hept-5-enoic acid isopropyl ester (42i)

Acid 15i from Example 24 (17 mg, 0.04 mmol) was converted into 15 mg (80%) of the title compound (42i) in accordance with the procedure of Example 67.

EXAMPLE 70

(Z)-7-[(1R,2S,3R,5R)-5-Chloro-2-(3,5-dimethyl-phenoxymethyl)-3-hydroxy-cyclopentyl]-hept-5-enoic acid isopropyl ester (42u)

Acid 15u from Example 36 (47 mg, 0.13 mmol) was converted into the title compound (42u) in accordance with the procedure of Example 67.

EXAMPLE 71

(Z)-7-[(1R,2S,3R,5R)-5-Chloro-3-hydroxy-2-(4-hydroxymethyl-phenoxymethyl)-cyclopentyl]-hept-5-enoic acid isopropyl ester (42bb)

Step 1: Acid 15aa from Example 42 (10 mg, 0.026 mmol) was converted into 6.5 mg (59%) of isopropyl ester 42aa in accordance with the procedure of Example 67.

Step 2: Aldehyde 42aa (6.5 mg, 0.015 mmol) was converted into 5.4 mg (83%) of the title compound (42bb) in accordance with the procedure of Example 43, step 1.

Binding Data

Ki

Competition binding experiments were performed in a medium containing Hank's balanced salt solution, Hepes 20 mM, pH 7.3, membranes (~60 μg protein) or $2\times10^5$ cells from HEK 293 cells stably expressing human EP2 receptors, [$^3$H] PGE2 (10 nM) and various concentrations of test compounds in a total volume of 300 μl. Reaction mixtures were incubated at 23° C. for 60 min, and were filtered over Whatman GF/B filters under vacuum. Filters were washed three times with 5 ml ice-cold buffer containing 50 mM Tris/HCl (pH 7.3). Non-specific binding was estimated in the presence of excess unlabeled PGE2 (10 μM). Binding data fitted to the binding model for a single class of binding sites, using nonlinear regression analysis. $IC_{50}$ values thus obtained were converted to Ki using the equation of $Ki=(IC_{50}/(1+[L]/K_D)$ where [L] represents PGE2 concentration (10 nM) and $K_D$ the dissociation constant for [$^3$H]PGE2 at human EP2 receptors (40 nM).

Radioligand Binding

Cells Stably Expressing $EP_1$, $EP_2$, $EP_4$ and FP Receptors

HEK-293 cells stably expressing the human or feline FP receptor, or $EP_1$, $EP_2$, or $EP_4$ receptors were washed with TME buffer, scraped from the bottom of the flasks, and homogenized for 30 sec using a Brinkman PT 10/35 polytron. TME buffer was added to achieve a final 40 ml volume in the centrifuge tubes (the composition of TME is 100 mM TRIS base, 20 mM $MgCl_2$, 2M EDTA; 10N HCl is added to achieve a pH of 7.4).

The cell homogenate was centrifuged at 19000 r.p.m. for 20 min at 4° C. using a Beckman Ti-60 rotor. The resultant pellet was resuspended in TME buffer to give a final 1 mg/ml protein concentration, as determined by Biorad assay. Radioligand binding competition assays vs. [3H-] 17-phenyl $PGF_2$, (5 nM) were performed in a 100 μl volume for 60 min. Binding reactions were started by adding plasma membrane fraction. The reaction was terminated by the addition of 4 ml ice-cold TRIS-HCl buffer and rapid filtration through glass fiber GF/B filters using a Brandel cell harvester. The filters were washed 3 times with ice-cold buffer and oven dried for one hour.

[$^3$H-] $PGE_2$ (specific activity 180 Ci mmol) was used as the radioligand for EP receptors. [$^3$H] 17-phenyl $PGF_2$, was employed for FP receptor binding studies. Binding studies employing $EP_1$, $EP_2$, $EP_4$ and FP receptors were performed in duplicate in at least three separate experiments. A 200 1 1 assay volume was used. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Competition studies were performed using a final concentration of 5 nM [$^3$H]-$PGE_2$, or 5 nM [$^3$H] 17-phenyl $PGF_2$, and non-specific binding determined with $10^{-5}$ M of unlabeled $PGE_2$, or 17-phenyl $PGF_{2\alpha}$, according to receptor subtype studied.

Methods for FLIPR™ Studies (a) Cell Culture

HEK-293(EBNA) cells, stably expressing one type or subtype of recombinant human prostaglandin receptors (prostaglandin receptors expressed: hDP/Gqs5; $hEP_1$; $hEP_2$/Gqs5; $hEP_{3A}$/Gqi5; $hEP_4$/Gqs5; hFP; hIP; hTP), were cultured in 100 mm culture dishes in high-glucose DMEM medium containing 10% fetal bovine serum, 2 mM 1-glutamine, 250 μg/ml geneticin (G418) and 200 μg/ml hygromycin B as selection markers, and 100 units/ml penicillin G, 100 μg/ml streptomycin and 0.25 μg/ml amphotericin B.

(b) Calcium Signal Studies on the FLIPR™

Cells were seeded at a density of $5\times10^4$ cells per well in Biocoat® Poly-D-lysine-coated black-wall, clear-bottom 96-well plates (Becton-Dickinson) and allowed to attach overnight in an incubator at 37° C. Cells were then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 μM, plates were washed four times with HBSS-HEPES buffer to remove excess dye leaving 100 μl in each well. Plates were re-equilibrated to 37° C. for a few minutes.

Cells were excited with an Argon laser at 488 nm, and emission was measured through a 510-570 nm bandwidth emission filter (FLIPR™, Molecular Devices, Sunnyvale, Calif.). Drug solution was added in a 50 μl volume to each well to give the desired final concentration. The peak increase in fluorescence intensity was recorded for each well. On each plate, four wells each served as negative (HBSS-HEPES buffer) and positive controls (standard agonists: BW245C (hDP); $PGE_2$ ($hEP_1$; $hEP_2$/Gqs5; $hEP_{3A}$/Gqi5; $hEP_4$/Gqs5); $PGF_{2\alpha}$ (hFP); carbacyclin (hIP); U-46619 (hTP), depending on receptor). The peak fluorescence change in each drug-containing well was then expressed relative to the controls.

Compounds were tested in a high-throughput (HTS) or concentration-response (CoRe) format. In the HTS format, forty-four compounds per plate were examined in duplicates at a concentration of $10^{-5}$ M. To generate concentration-response curves, four compounds per plate were tested in duplicates in a concentration range between $10^{-5}$ and $10^{-11}$ M. The duplicate values were averaged. In either, HTS or CoRe format each compound was tested on at least 3 separate plates using cells from different passages to give an $n \geq 3$.

The results of the binding and activity studies, presented in Table 1 demonstrate that the compounds disclosed herein are selective prostaglandin $EP_2$ agonists, and are thus useful for the treatment of glaucoma, ocular hypertension, the other diseases or conditions disclosed herein.

In Vivo Examples (Z)-7-[(1R,2S,3R,5R)-5-Chloro-2-(3,5-dichloro-phenoxymethyl)-3-hydroxy-cyclopentyl]-hept-5-enoic acid (15b) was tested at multiple concentrations in normotensive dogs, dosing once daily for 5 days. At 0.05%, the maximum IOP decrease from baseline was 4.3 mmHg (30%) at 6 h; the maximum OSH score was 0.6 at 6 h. At 0.1%, the maximum IOP decrease from baseline was 4.8 mmHg (34%) at 102 h; the maximum OSH score was 1.3 at 6 h. This compound was also tested in laser-induced hypertensive monkeys, using one single day dose. At 0.1%, the maximum IOP decrease from baseline was 6 mmHg (19%) at 6 h.

(Z)-7-[(1R,2S,3R,5R)-5-Chloro-2-(3,5-dichloro-phenoxymethyl)-3-hydroxy-cyclopentyl]-hept-5-enoic acid isopropyl ester (42b) was tested in normotensive dogs at 0.05%, dosing once daily for 5 days. The maximum intraocular pressure (IOP) decrease from baseline was 3 mmHg (19%) at 6 h; the maximum ocular surface hyperemia (OSH) score was 0.6 at 74 h. This compound was also tested in laser-induced hypertensive monkeys, using one single day dose. At 0.01%, the maximum IOP decrease from baseline was 6 mmHg (16%) at 6 h.

(Z)-7-[(1R,2S,3R,5R)-2-(3,5-Bis-trifluoromethyl-phenoxymethyl)-5-chloro-3-hydroxy-cyclopentyl]-hept-5-enoic acid (15c) was tested in normotensive dogs at 0.1%, dosing once daily for 5 days. The maximum intraocular pressure (IOP) decrease from baseline was 4.8 mmHg (35%) at 100 h; the maximum ocular surface hyperemia (OSH) score was 0.9 at 52 h. This compound was also tested in laser-induced hypertensive monkeys, using one single day dose. At 0.1%, the maximum IOP decrease from baseline was 11 mmHg (30%) at 6 h.

(Z)-7-[(1R,2S,3R,5R)-2-(3,5-Bis-trifluoromethyl-phenoxymethyl)-5-chloro-3-hydroxy-cyclopentyl]-hept-5-enoic acid isopropyl ester (42c) was tested in normotensive dogs at 0.03%, dosing once daily for 5 days. The maximum intraocular pressure (IOP) decrease from baseline was 2.3 mmHg (14%) at 100 h; the maximum ocular surface hyperemia (OSH) score was 0.7 at 78 h. This compound was also tested in laser-induced hypertensive monkeys, using one single day dose. At 0.03%, the maximum IOP decrease from baseline was 4 mmHg (11%) at 6 h.

(Z)-7-[(1R,2S,3R,5R)-5-Chloro-3-hydroxy-2-(naphthalen-1-yloxymethyl)-cyclopentyl]-hept-5-enoic acid (15e) was tested in normotensive dogs at 0.1%, dosing once daily for 5 days. The maximum intraocular pressure (IOP) decrease from baseline was 5.8 mmHg (41%) at 6 h; the maximum ocular surface hyperemia (OSH) score was 0.8 at 54 h. This compound was also tested in laser-induced hypertensive monkeys, using one single day dose. At 0.1%, the maximum IOP decrease from baseline was 11.8 mmHg (31%) at 6 h.

(Z)-7-[(1R,2S,3R,5R)-5-Chloro-2-(3,5-dimethyl-phenoxymethyl)-3-hydroxy-cyclopentyl]-hept-5-enoic acid (15u) was tested in normotensive dogs at 0.1%, dosing once daily for 5 days. The maximum intraocular pressure (IOP) decrease from baseline was 6.5 mmHg (46%) at 52 h; the maximum ocular surface hyperemia (OSH) score was 1.2 at 28 h. This compound was also tested in laser-induced hypertensive monkeys, using one single day dose. At 0.1%, the maximum IOP decrease from baseline was 9 mmHg (25%) at 2 h.

(Z)-7-[(1R,2S,3R,5R)-5-Chloro-2-(3,5-dimethyl-phenoxymethyl)-3-hydroxy-cyclopentyl]-hept-5-enoic acid isopropyl ester (42u) was tested in normotensive dogs at 0.1%, dosing once daily for 5 days. The maximum intraocular pressure (IOP) decrease from baseline was 4.3 mmHg (30%) at 30 h; the maximum ocular surface hyperemia (OSH) score was 0.9 at 74 h. This compound was also tested in laser-induced hypertensive monkeys, using one single day dose. At 0.1%, the maximum IOP decrease from baseline was 8 mmHg (23%) at 6 h.

(Z)-7-[(1R,2S,3R,5R)-5-Chloro-3-hydroxy-2-(3-trifluoromethyl-phenoxymethyl)-cyclopentyl]-hept-5-enoic acid (15i) was tested in normotensive dogs at 0.1%, dosing once daily for 5 days. The maximum intraocular pressure (IOP) decrease from baseline was 2.5 mmHg (16%) at 78 h; the maximum ocular surface hyperemia (OSH) score was 0.5 at 6 h. This compound was also tested in laser-induced hypertensive monkeys, using one single day dose. At 0.1%, the maximum IOP decrease from baseline was 10.8 mmHg (28%) at 6 h.

(Z)-7-[(1R,2S,3R,5R)-5-Chloro-3-hydroxy-2-(3-trifluoromethyl-phenoxymethyl)-cyclopentyl]-hept-5-enoic acid isopropyl ester (42i) was tested in normotensive dogs at 0.1%, dosing once daily for 5 days. The maximum intraocular pressure (IOP) decrease from baseline was 2.7 mmHg (19%) at 2 h; the maximum ocular surface hyperemia (OSH) score was 0.6 at 50 h. This compound was also tested in laser-induced hypertensive monkeys, using one single day dose. At 0.1%, the maximum IOP decrease from baseline was 4.7 mmHg (14%) at 6 h.

(Z)-7-[(1R,2S,3R,5R)-5-Chloro-3-hydroxy-2-(4-hydroxymethyl-phenoxymethyl)-cyclopentyl]-hept-5-enoic acid (15bb) was tested in normotensive dogs at 0.1%, dosing once daily for 5 days. The maximum intraocular pressure (IOP) decrease from baseline was 2.8 mmHg (20%) at 98 h; the maximum ocular surface hyperemia (OSH) score was 0.6 at 98 h. This compound was also tested in laser-induced hypertensive monkeys, using one single day dose. At 0.1%, the maximum IOP decrease from baseline was 2 mmHg (6%) at 6 h.

(Z)-7-[(1R,2S,3R,5R)-5-Chloro-3-hydroxy-2-(4-hydroxymethyl-phenoxymethyl)-cyclopentyl]-hept-5-enoic acid isopropyl ester (42bb) was tested in normotensive dogs at 0.1%, dosing once daily for 5 days. The maximum intraocular pressure (IOP) decrease from baseline was 4.6 mmHg (33%) at 100 h; the maximum ocular surface hyperemia (OSH) score was 0.6 at 30 h. This compound was also tested in laser-induced hypertensive monkeys, using one single day dose. At 0.1%, the maximum IOP decrease from baseline was 5.5 mmHg (16%) at 6 h.

What is claimed is:

1. A method of treating a disease or condition selected from: glaucoma, ocular hypertension, and baldness, comprising administering an effective amount of a compound to a mammal in need thereof, said compound having one of the formulas shown below:

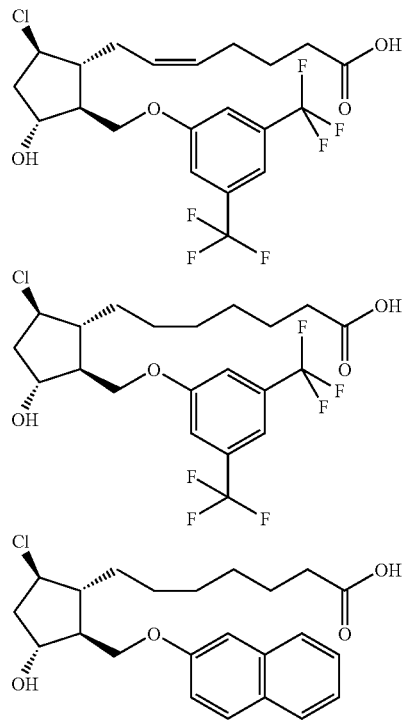

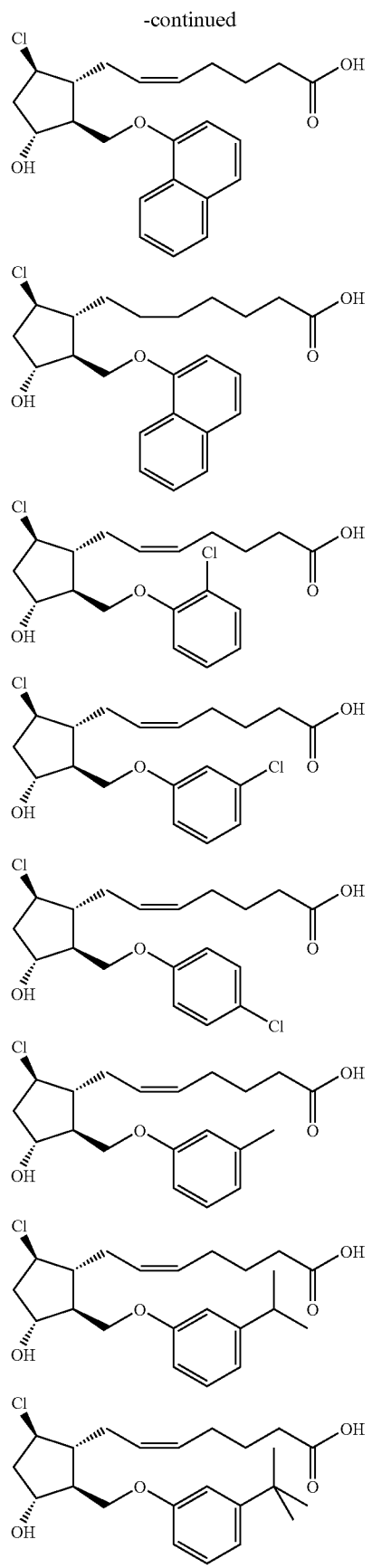
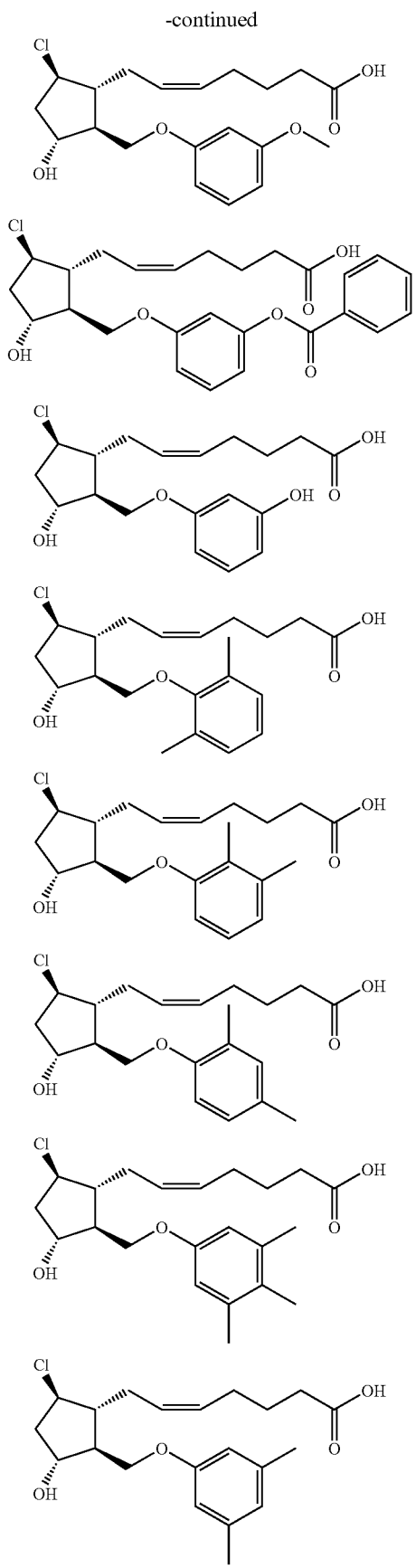

71
-continued
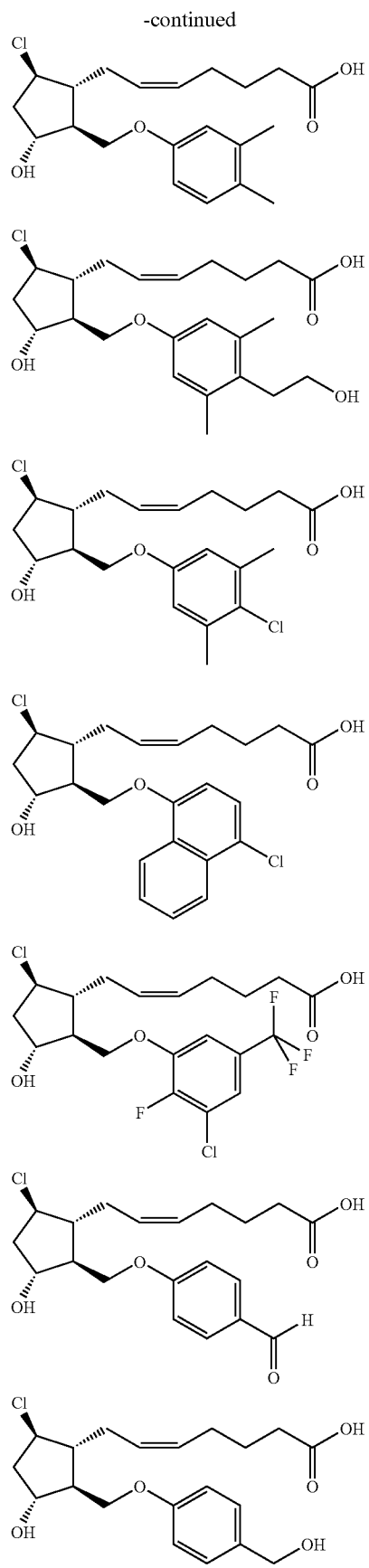
72
-continued
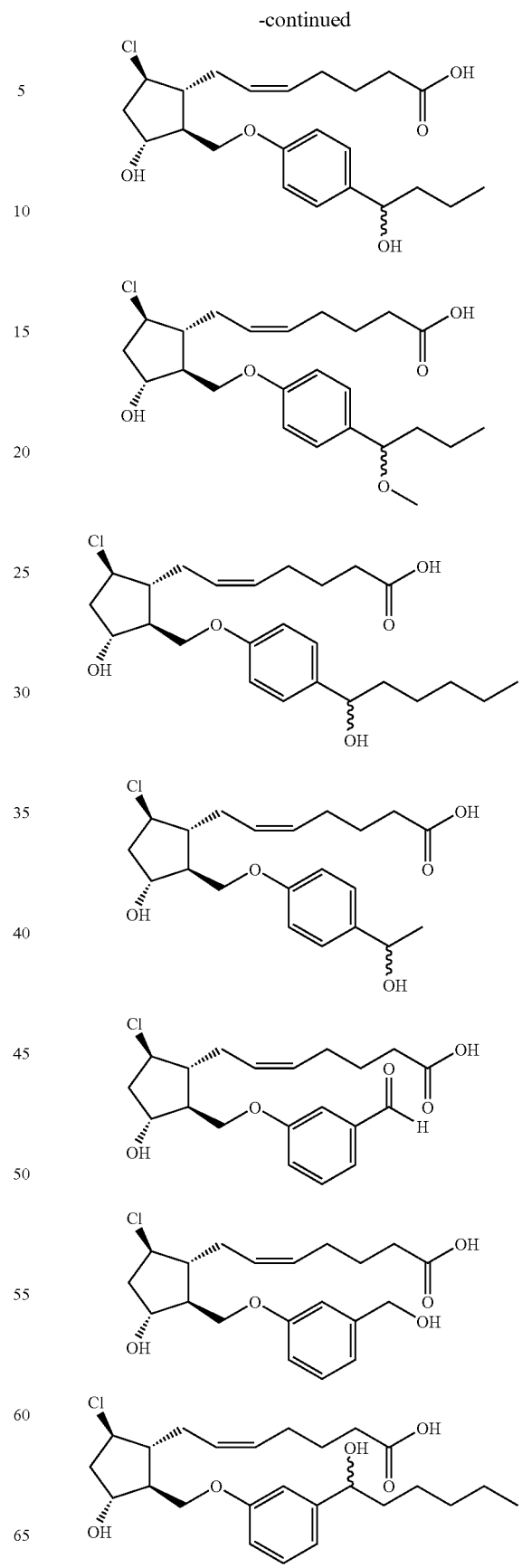

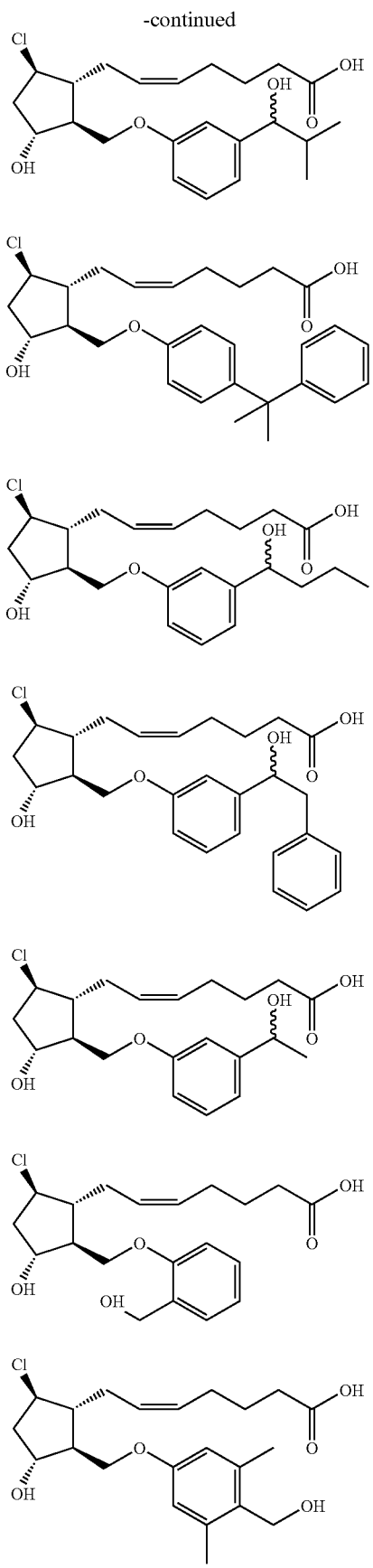
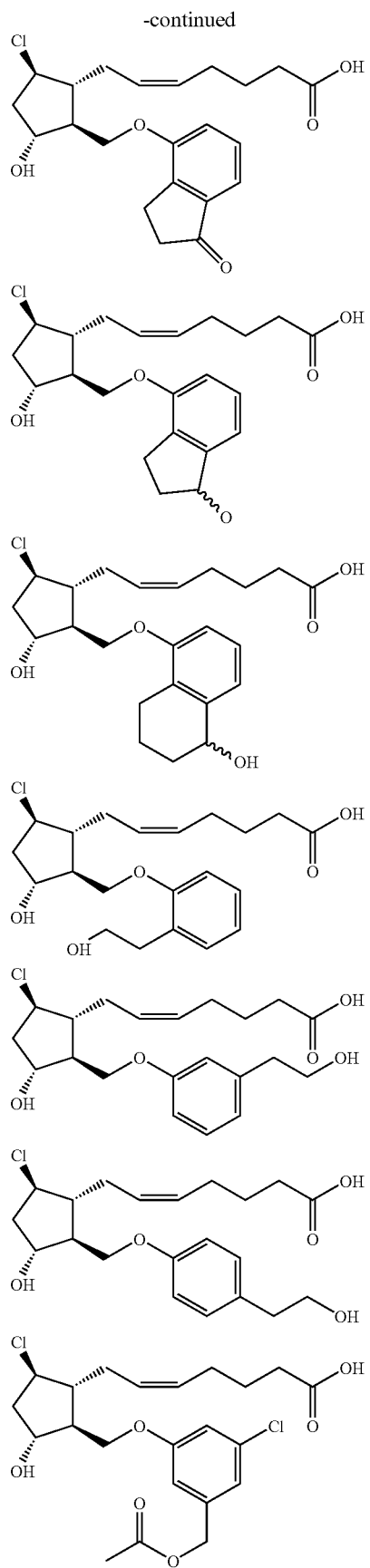

-continued

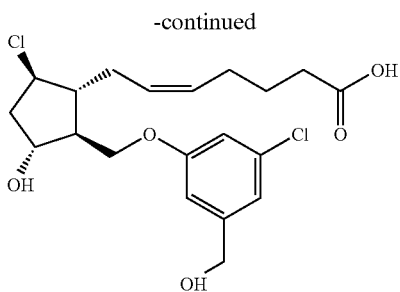

or a pharmaceutically acceptable salt or a prodrug thereof.

2. The method of claim 1 wherein the compound has the formula

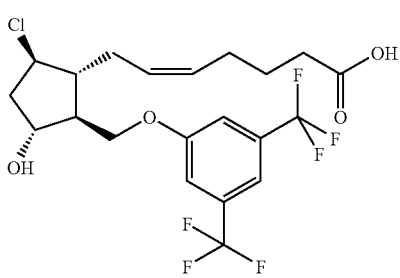

or a pharmaceutically acceptable salt or a prodrug thereof.

3. The method of claim 1 wherein the compound has the formula

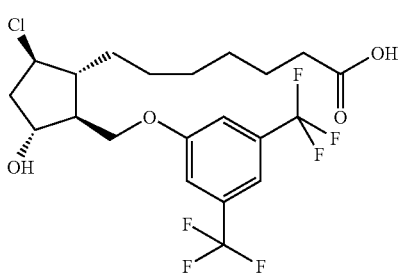

or a pharmaceutically acceptable salt or a prodrug thereof.

4. The method of claim 1 wherein the compound has the formula

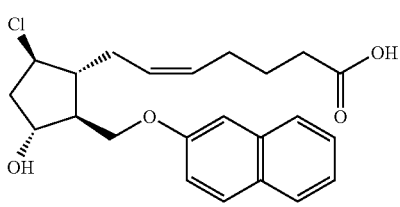

or a pharmaceutically acceptable salt or a prodrug thereof.

5. The method of claim 1 wherein the compound has the formula

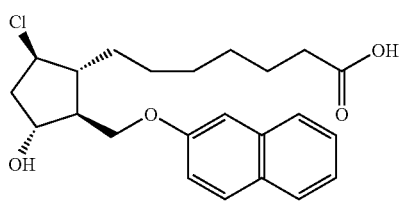

or a pharmaceutically acceptable salt or a prodrug thereof.

6. The method of claim 1 wherein the compound has the formula

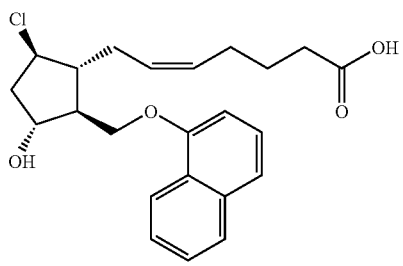

or a pharmaceutically acceptable salt or a prodrug thereof.

7. The method of claim 1 wherein the compound has the formula

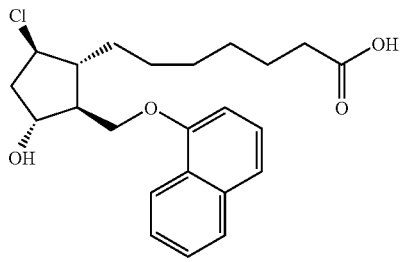

or a pharmaceutically acceptable salt or a prodrug thereof.

8. The method of claim 1 wherein the compound has the formula

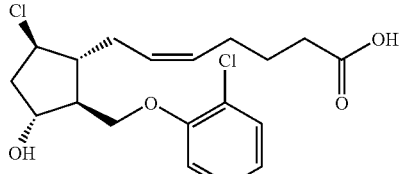

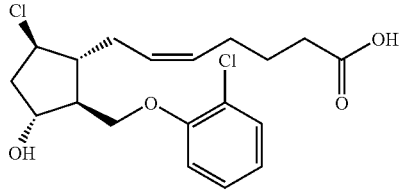

or a pharmaceutically acceptable salt or a prodrug thereof.

9. The method of claim 1 wherein the compound has the formula

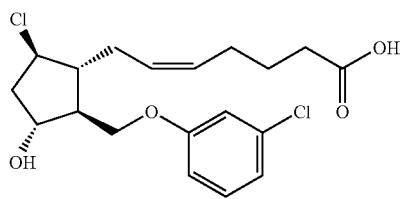

or a pharmaceutically acceptable salt or a prodrug thereof.

10. The method of claim 1 wherein the compound has the formula

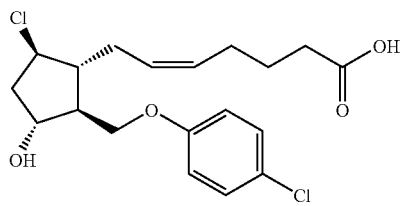

or a pharmaceutically acceptable salt or a prodrug thereof.

11. The method of claim 1 wherein the compound has the formula

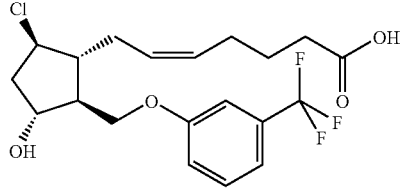

or a pharmaceutically acceptable salt or a prodrug thereof.

12. The method of claim 1 wherein the compound has the formula

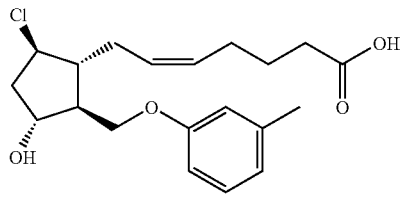

or a pharmaceutically acceptable salt or a prodrug thereof.

13. The method of claim 1 wherein the compound has the formula

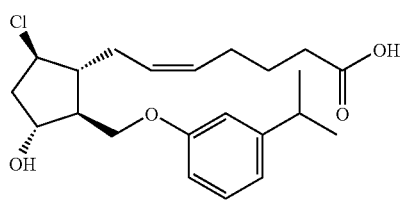

or a pharmaceutically acceptable salt or a prodrug thereof.

14. The method of claim 1 wherein the compound has the formula

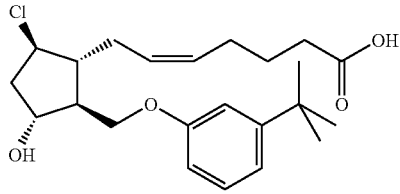

or a pharmaceutically acceptable salt or a prodrug thereof.

15. The method of claim 1 wherein the compound has the formula

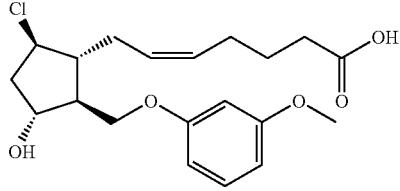

or a pharmaceutically acceptable salt or a prodrug thereof.

16. The method of claim 1 wherein the compound has the formula

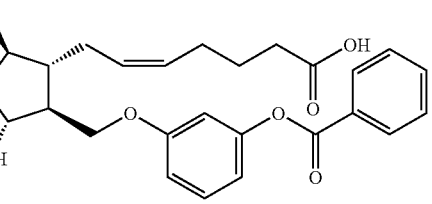

or a pharmaceutically acceptable salt or a prodrug thereof.

17. The method of claim 1 wherein the compound has the formula

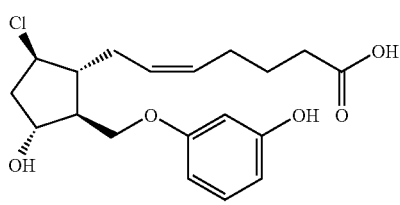

or a pharmaceutically acceptable salt or a prodrug thereof.

18. The method of claim 1 wherein the compound has the formula

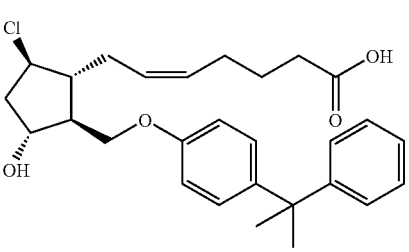

or a pharmaceutically acceptable salt or a prodrug thereof.

19. The method of claim 1 wherein the compound has the formula

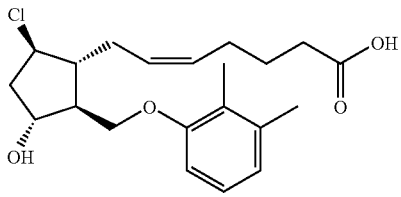

or a pharmaceutically acceptable salt or a prodrug thereof.

20. The method of claim 1 wherein the compound has the formula

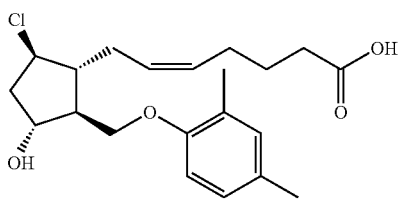

or a pharmaceutically acceptable salt or a prodrug thereof.

21. The method of claim 1 wherein the mammal is a human.

22. The method of claim 21 wherein the disease or condition is glaucoma.

23. The method of claim 21 wherein the disease or condition is ocular hypertension.

24. The method of claim 21 wherein the disease or condition is baldness.

* * * * *